United States Patent
Kim et al.

(10) Patent No.: US 10,367,155 B2
(45) Date of Patent: Jul. 30, 2019

(54) ORGANOMETALLIC COMPLEX AND ORGANIC LIGHT-EMITTING DIODE INCLUDING THE SAME

(71) Applicants: SAMSUNG DISPLAY CO., LTD., Yongin, Gyeonggi-Do (KR); PUSAN NATIONAL UNIVERSITY INDUSTRY-UNIVERSITY COOPERATION FOUNDATION, Busan (KR)

(72) Inventors: Soung-Wook Kim, Yongin (KR); Jae-Hong Kim, Yongin (KR); Myeong-Suk Kim, Yongin (KR); Moon-Jae Lee, Yongin (KR); Young-Inn Kim, Yongin (KR); Seong-Jae Yun, Yongin (KR); Dae-Young Kim, Yongin (KR)

(73) Assignees: SAMSUNG DISPLAY CO., LTD., Yongin, Gyeonggi-Do (KR); PUSAN NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 736 days.

(21) Appl. No.: 13/948,649

(22) Filed: Jul. 23, 2013

(65) Prior Publication Data
US 2014/0225076 A1 Aug. 14, 2014

(30) Foreign Application Priority Data
Feb. 13, 2013 (KR) .................. 10-2013-0015533

(51) Int. Cl.
| | | |
|---|---|---|
| *H01L 51/54* | (2006.01) | |
| *C09K 11/06* | (2006.01) | |
| *H01L 51/00* | (2006.01) | |
| *C07F 15/00* | (2006.01) | |
| *H05B 33/14* | (2006.01) | |
| *H01L 51/50* | (2006.01) | |

(52) U.S. Cl.
CPC ...... *H01L 51/0085* (2013.01); *C07F 15/0033* (2013.01); *C09K 11/06* (2013.01); *H05B 33/14* (2013.01); *C09K 2211/1007* (2013.01); *C09K 2211/1014* (2013.01); *C09K 2211/1029* (2013.01); *C09K 2211/1044* (2013.01); *C09K 2211/185* (2013.01); *H01L 51/0042* (2013.01); *H01L 51/5016* (2013.01); *H01L 2051/0063* (2013.01); *H01L 2251/5384* (2013.01)

(58) Field of Classification Search
None
See application file for complete search history.

(56) References Cited

U.S. PATENT DOCUMENTS

| | | | |
|---|---|---|---|
| 7,329,898 B2 | 2/2008 | Igarashi | |
| 2001/0015432 A1* | 8/2001 | Igarashi | C09K 11/06 257/1 |
| 2001/0019782 A1* | 9/2001 | Igarashi et al. | C07F 15/0033 428/690 |
| 2002/0024293 A1* | 2/2002 | Igarashi et al. | C07F 15/0033 313/483 |
| 2002/0034656 A1 | 3/2002 | Thompson et al. | |
| 2002/0190250 A1* | 12/2002 | Grushin et al. | C07D 213/26 257/40 |
| 2004/0137267 A1* | 7/2004 | Igarashi et al. | C09K 11/06 428/690 |
| 2004/0137268 A1* | 7/2004 | Igarashi et al. | C09K 11/06 428/690 |
| 2004/0265633 A1* | 12/2004 | Son et al. | C07F 15/0033 428/690 |
| 2007/0138437 A1* | 6/2007 | Haga et al. | C07F 15/0033 252/301.16 |

(Continued)

FOREIGN PATENT DOCUMENTS

| | | |
|---|---|---|
| KR | 10-2009-0122930 A | 12/2009 |
| KR | 10-2010-0110958 A | 10/2010 |

(Continued)

OTHER PUBLICATIONS

Jirasko et al., "Structural Analysis of Organometallic Compounds With Soft Ionization Mass Spectrometry", Mass Spectrometry Reviews, vol. 30, pp. 1013-1036 (2011).*

"Introduction to Mass Spectrometry", The University of Arizona Department of Chemistry [online; 6 pages, retrieved on Nov. 2, 2017]. Retrieved from the Internet:<URL: http://cbc.arizona.edu/massspec/intro_html/intro.html>.*

"Atmospheric-pressure chemical ionization", Wikipedia [online; 5 pages, retrieved on Nov. 30, 2017]. Retrieved from the Internet:<URL: https://en.wikipedia.org/wiki/Atmospheric-pressure_chemical_ionization>.*

(Continued)

*Primary Examiner* — Marie R. Yamnitzky
(74) *Attorney, Agent, or Firm* — Lee & Morse, P.C.

(57) ABSTRACT

An organometallic complex and an organic light-emitting diode including the same, the organometallic complex being represented by Formula 1 below:

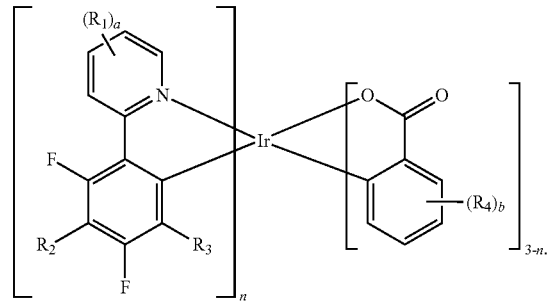

11 Claims, 3 Drawing Sheets

(56) References Cited

U.S. PATENT DOCUMENTS

2007/0292713 A9  12/2007  Dobbs et al.
2010/0171111 A1   7/2010  Takada et al.

FOREIGN PATENT DOCUMENTS

KR      10-1066743 B1    9/2011
WO    WO 2010/093176 A2  8/2010

OTHER PUBLICATIONS

Soo Bong Han, Transition Metal-Catalyzed Reductive C—C Bond Forming Hydrogenation/Transfer Hydrogenation and Applications in the Total Synthesis of (+)-Roxaticin, The University of Texas at Austin, 2010, Dissertation (447 pages).

\* cited by examiner

ORGANOMETALLIC COMPLEX AND ORGANIC LIGHT-EMITTING DIODE INCLUDING THE SAME

CROSS-REFERENCE TO RELATED PATENT APPLICATION

Korean Patent Application No. 10-2013-0015533, filed on Feb. 13, 2013, in the Korean Intellectual Property Office, is incorporated herein its entirety by reference.

BACKGROUND

1. Field

Embodiments relate to an organometallic complex and an organic light-emitting diode including the same.

2. Description of the Related Art

Organic light-emitting diode (OLEDs), which are self-emitting diodes, have advantages such as wide viewing angles, excellent contrast, quick response, high brightness, and excellent driving voltage characteristics, and can provide multicolored images.

SUMMARY

The embodiments provide a high-quality organic light-emitting diode.

Additional aspects will be set forth in part in the description which follows and, in part, will be apparent from the description, or may be learned by practice of the presented embodiments.

According to an embodiment, there is provided an organometallic complex represented by Formula 1 below:

<Formula 1>

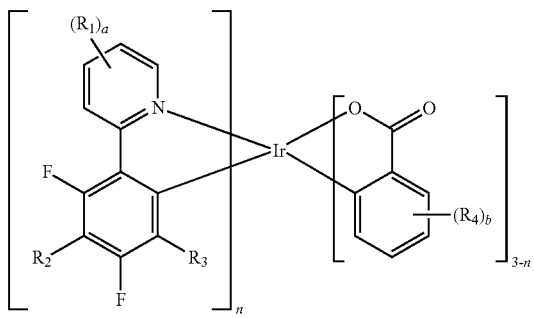

in Formula 1, $R_1$ to $R_4$ are each independently selected from a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group, $-N(Q_1)(Q_2)$, $-C(=O)(Q_3)$, and $-Si(Q_4)(Q_5)(Q_6)$ (wherein $Q_1$ to $Q_6$ are each independently a hydrogen atom, a substituted or unsubstituted $C_1$-$C_{60}$ alkyl group, a substituted or unsubstituted $C_6$-$C_{30}$ aryl group, or a substituted or unsubstituted $C_2$-$C_{30}$ heteroaryl group);

a and b are each independently an integer from 1 to 4, for example, when a is 2 or greater, 2 or more $R_1$s may be identical to or different from each other, and two or more $R_1$s are optionally bound to each other so as to form a saturated or unsaturated ring. Likewise, when b is 2 or greater, 2 or more $R_4$s may be identical to or different to each other; and n is 1 or 2.

According to another embodiment, there is provided an organic light-emitting diode including a substrate, a first electrode, a second electrode disposed opposite to the first electrode, and an organic layer that is disposed between the first electrode and the second electrode and includes an emission layer, wherein the organic layer includes one or more of the organometallic complex.

BRIEF DESCRIPTION OF THE DRAWINGS

The above and other features and advantages will become more apparent by describing in detail exemplary embodiments thereof with reference to the attached drawings in which.

DETAILED DESCRIPTION

Figure 1:
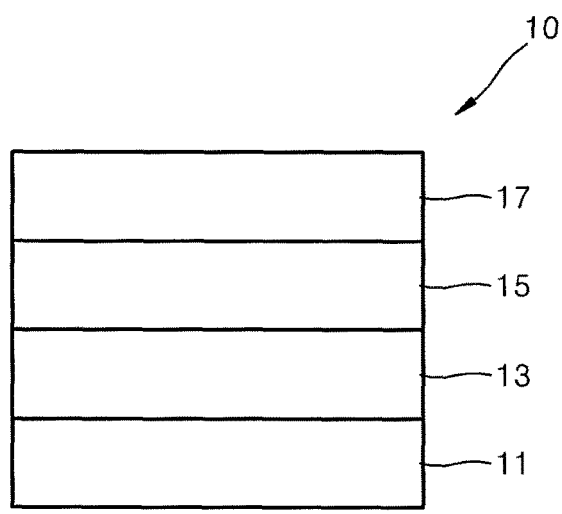
FIG. 1 illustrates a cross-sectional view of a structure of an organic light-emitting diode according to an embodiment.

As used herein, the term "and/or" includes any and all combinations of one or more of the associated listed items. Expressions such as "at least one of," when preceding a list of elements, modify the entire list of elements and do not modify the individual elements of the list. For example, when a variable is indicated as being "independently selected from" a list including i), ii), iii), etc., the variable may be only one, or more than one, selected from any of the elements of any of i), ii), iii), etc.

An organometallic complex according to an embodiment is represented by Formula 1 below:

<Formula 1>

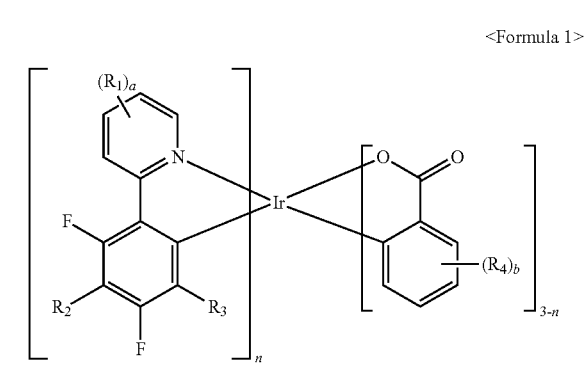

in Formula 1, $R_1$ to $R_4$ are each independently selected from a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group, $—N(Q_1)(Q_2)$, $—C(=O)(Q_3)$, and $—Si(Q_4)(Q_5)(Q_6)$ (wherein $Q_1$ to $Q_6$ are each independently a hydrogen atom, a substituted or unsubstituted $C_1$-$C_{60}$ alkyl group, a substituted or unsubstituted $C_6$-$C_{30}$ aryl group, or a substituted or unsubstituted $C_2$-$C_{30}$ heteroaryl group).

For example, $R_1$ to $R_4$ in Formula 1 are each independently selected from:
i) a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, a phosphoric acid or a salt thereof, a $C_1$-$C_{20}$ alkyl group, and a $C_1$-$C_{20}$ alkoxy group;
ii) a $C_1$-$C_{20}$ alkyl group and a $C_1$-$C_{20}$ alkoxy group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, and a phosphoric acid or a salt thereof;
iii) a $C_6$-$C_{14}$ aryl group and a $C_2$-$C_{14}$ heteroaryl group;
iv) a $C_6$-$C_{14}$ aryl group and a $C_2$-$C_{14}$ heteroaryl group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group, a $C_6$-$C_{14}$ aryl group, and a $C_2$-$C_{14}$ heteroaryl group,
v) $—N(Q_1)(Q_2)$; and
vi) $—C(=O)(Q_3)$;
wherein $Q_1$ to $Q_3$ are each independently selected from:
i) a hydrogen atom, a $C_1$-$C_{20}$ alkyl group, and a $C_1$-$C_{20}$ alkoxy group;
ii) a $C_1$-$C_{20}$ alkyl group and a $C_1$-$C_{20}$ alkoxy group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, and a phosphoric acid or a salt thereof;
iii) a $C_6$-$C_{14}$ aryl group and a $C_2$-$C_{14}$ heteroaryl group; and
iv) a $C_6$-$C_{14}$ aryl group and a $C_2$-$C_{14}$ heteroaryl group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group, a $C_6$-$C_{14}$ aryl group, and a $C_2$-$C_{14}$ heteroaryl group.

According to an embodiment, $R_1$ to $R_4$ in Formula 1 are each independently selected from:
i) a hydrogen atom, a deuterium atom, F, Cl, a hydroxyl group, a cyano group, a nitro group, an amino group, an amidino group, a hydrazine, a hydrazone, a carboxyl group or a salt thereof, a sulfonic acid or a salt thereof, a phosphoric acid or a salt thereof, a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, and a tert-decanyl group;
ii) a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, and a tert-decanyl group, each substituted with at least one of a deuterium atom, F, Cl, a hydroxyl group, a cyano group, a nitro group, an amino group, an amidino group, a hydrazine, a hydrazone, a carboxyl group or a salt thereof, a sulfonic acid or a salt thereof, and a phosphoric acid or a salt thereof;
iii) a phenyl group, a naphthyl group, an anthryl group, a pyrenyl group, a phenanthrenyl group, a fluorenyl group, a pyridinyl group, a pyrazinyl group, a pyrimidinyl group, a triazinyl group, a quinolinyl group, an isoquinolinyl group, a quinoxalinyl group, a phenanthrolinyl group, and a carbazolyl group;
iv) a phenyl group, a naphthyl group, an anthryl group, a pyrenyl group, a phenanthrenyl group, a fluorenyl group, a pyridinyl group, a pyrazinyl group, a pyrimidinyl group, a triazinyl group, a quinolinyl group, an isoquinolinyl group, a quinoxalinyl group, a phenanthrolinyl group, and a carbazolyl group, each substituted with at least one of a deuterium atom, F, Cl, a hydroxyl group, a cyano group, a nitro group, an amino group, an amidino group, a hydrazine, a hydrazone, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthryl group, a pyrenyl group, a phenanthrenyl group, a fluorenyl group, a pyridinyl group, a pyrazinyl group, a pyrimidinyl group, a triazinyl group, a quinolinyl group, an isoquinolinyl group, a quinoxalinyl group, a phenanthrolinyl group, and a carbazolyl group;
v) $—N(Q_1)(Q_2)$; and
vi) $—C(=O)(Q_3)$;
wherein $Q_1$ to $Q_3$ are each independently selected from:
i) a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, and a tert-decanyl group;
ii) a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, and a tert-decanyl group, each substituted with at least one of a deuterium atom, F, Cl, a hydroxyl group, a cyano group, a nitro group, an amino group, an amidino group, a hydrazine, a hydrazone, a carboxyl group or a salt thereof, a sulfonic acid or a salt thereof, and a phosphoric acid or a salt thereof;

iii) a phenyl group, a naphthyl group, an anthryl group, a pyrenyl group, a phenanthrenyl group, a fluorenyl group, a pyridinyl group, a pyrazinyl group, a pyrimidinyl group, a triazinyl group, a quinolinyl group, an isoquinolinyl group, a quinoxalinyl group, a phenanthrolinyl group, and a carbazolyl group; and iv) a phenyl group, a naphthyl group, an anthryl group, a pyrenyl group, a phenanthrenyl group, a fluorenyl group, a pyridinyl group, a pyrazinyl group, a pyrimidinyl group, a triazinyl group, a quinolinyl group, an isoquinolinyl group, a quinoxalinyl group, a phenanthrolinyl group, and a carbazolyl group, each substituted with at least one of a deuterium atom, F, Cl, a hydroxyl group, a cyano group, a nitro group, an amino group, an amidino group, a hydrazine, a hydrazone, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthryl group, a pyrenyl group, a phenanthrenyl group, a fluorenyl group, a pyridinyl group, a pyrazinyl group, a pyrimidinyl group, a triazinyl group, a quinolinyl group, an isoquinolinyl group, a quinoxalinyl group, a phenanthrolinyl group, and a carbazolyl group.

In some embodiments, $R_1$ in Formula 1 is selected from a hydrogen atom, a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, a tert-decanyl group, a phenyl group, a naphthyl group, an anthryl group, a pyrenyl group, a phenanthrenyl group, a fluorenyl group, a pyridinyl group, a pyrazinyl group, a pyrimidinyl group, a triazinyl group, a quinolinyl group, an isoquinolinyl group, a quinoxalinyl group, a phenanthrolinyl group, a carbazolyl group, and —N($Q_1$)($Q_2$) (wherein $Q_1$ to $Q_3$ are each independently a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, a tert-decanyl group 기], a phenyl group, a naphthyl group, an anthryl group, a pyrenyl group, a phenanthrenyl group, a fluorenyl group, a pyridinyl group, a pyrazinyl group, a pyrimidinyl group, a triazinyl group, a quinolinyl group, an isoquinolinyl group, a quinoxalinyl group, a phenanthrolinyl group, and a carbazolyl group), but is not limited thereto.

In some embodiments, $R_1$ in Formula 1 is selected from a hydrogen atom, a methyl group, —N($Q_1$)($Q_2$) (wherein $Q_1$ and $Q_2$ are each independently a methyl group or a phenyl group), a pyridinyl group, a phenyl group, a naphthyl group, a quinolinyl group, and an isoquinolinyl group.

Also, $R_2$ in Formula 1 is selected from, i) a halogen atom, a cyano group, and a nitro group;

ii) a $C_1$-$C_{20}$ alkyl group substituted with at least one of a halogen atom and a $C_{20}$ alkyl group;

iii) a $C_6$-$C_{14}$ aryl group substituted with at least one of a halogen atom and a $C_{20}$ alkyl group; and iv) —C(=O)($Q_3$) (wherein $Q_3$ is selected from a $C_1$-$C_{20}$ alkyl group and a $C_6$-$C_{20}$ aryl group, each substituted with at least one halogen atom).

For example, $R_2$ in Formula 1 may be an electron withdrawing group. In some embodiments, $R_2$ in Formula 1 is selected from a halogen atom, a cyano group, and a nitro group; a $C_1$-$C_{20}$ alkyl group substituted with at least one halogen atom; and a $C_6$-$C_{14}$ aryl group substituted with at least one halogen atom, but is not limited thereto.

For example, $R_2$ in Formula 2 is selected from:

i) F, a cyano group, and a nitro group; and ii) a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, a tert-decanyl group, a phenyl group, a naphthyl group, an anthryl group, a pyrenyl group, a phenanthrenyl group, and a fluorenyl group substituted with at least one of F or a C1-C10 alkyl group, but is not limited thereto.

$R_3$ and $R_4$ in Formula 1 may be a hydrogen atom.

a and b in Formula 1 may be each independently an integer from 1 to 4. a in Formula 1 indicates the number of $R_1$, and when a is 2 or more, 2 or more of $R_1$s may be identical to or different from each other.

When a in Formula 1 is 2 or more, 2 or more of $R_1$s are optionally bound to each other to form a saturated or unsaturated ring (i.e., refer to Complex 15 which will be described later).

b in Formula 1 indicates a number of $R_4$, and when b is 2 or more, 2 or more of $R_4$s may be identical to or different from each other.

n in Formula 1 may be 1 or 2. For example, n in Formula may be 2, but is not limited thereto.

In some embodiments, the organometallic complex may be represented by Formula 1A or 1B below:

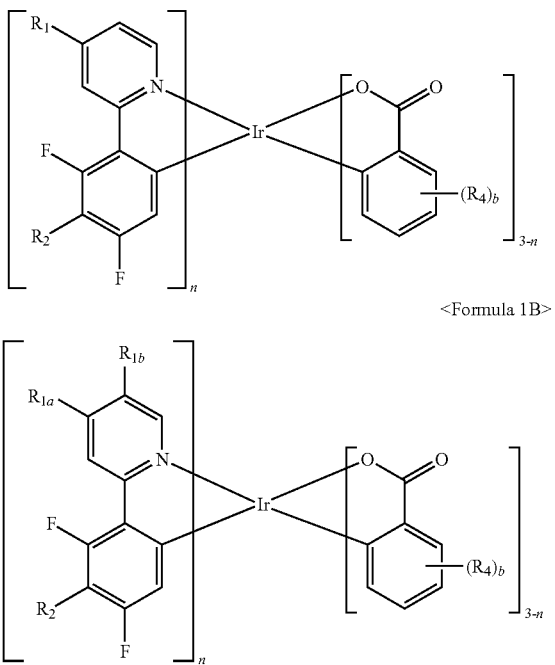

<Formula 1A>

<Formula 1B> in Formulas 1A and 1B, $R_1$, $R_2$, $R_4$, b and n are already defined above. Also, detailed descriptions about $R_{1a}$ and $R_{1b}$ in Formula 1B are each defined as described in $R_1$ above.

In some embodiments, the organometallic complex may be represented by Formula 1A, and R1 in Formula 1A is selected from:

a hydrogen atom, a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, a tert-decanyl group, a phenyl group, a naphthyl group, an anthryl group, a pyrenyl group, a phenanthrenyl group, a fluorenyl group, a pyridinyl group, a pyrazinyl group, a pyrimidinyl group, a triazinyl group, a quinolinyl group, an isoquinolinyl group, a quinoxalinyl group, a phenanthrolinyl group, a carbazolyl group, and —N($Q_1$)($Q_2$) (wherein $Q_1$ to $Q_3$ are each independently selected from a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, a tert-decanyl group, a phenyl group, a naphthyl group, an anthryl group, a pyrenyl group, a phenanthrenyl group, a fluorenyl group, a pyridinyl group, a pyrazinyl group, a pyrimidinyl group, a triazinyl group, a quinolinyl group, an isoquinolinyl group, a quinoxalinyl group, a phenanthrolinyl group, and a carbazolyl group), and $R_2$ is selected from:

i) F, a cyano group, and a nitro group; and ii) a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, a tert-decanyl group, a phenyl group, a naphthyl group, an anthryl group, a pyrenyl group, a phenanthrenyl group, and a fluorenyl group, each substituted with at least one of F or a $C_1$-$C_{10}$ alkyl group.

In some embodiments, the organometallic complex may be represented by Formula 1B, wherein in Formula 1B, $R_{1a}$ and $R_{1b}$ are each independently selected from a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, a tert-decanyl group, a phenyl group, a naphthyl group, an anthryl group, a pyrenyl group, a phenanthrenyl group, a fluorenyl group, a pyridinyl group, a pyrazinyl group, a pyrimidinyl group, a triazinyl group, a quinolinyl group, an isoquinolinyl group, a quinoxalinyl group, a phenanthrolinyl group, a carbazolyl group, and —N($Q_1$)($Q_2$) (wherein $Q_1$ to $Q_3$ are each independently selected from a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, a tert-decanyl group 7], a phenyl group, a naphthyl group, an anthryl group, a pyrenyl group, a phenanthrenyl group, a fluorenyl group, a pyridinyl group, a pyrazinyl group, a pyrimidinyl group, a triazinyl group, a quinolinyl group, an isoquinolinyl group, a quinoxalinyl group, a phenanthrolinyl group, and a carbazolyl group), and $R_2$ is selected from:

i) F, a cyano group, and a nitro group; and ii) a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, a tert-decanyl group, a phenyl group, a naphthyl group, an anthryl group, a pyrenyl group, a phenanthrenyl group, and a fluorenyl group, each substituted with at least one of F or a $C_1$-$C_{10}$ alkyl group.

In some other embodiments, the organometallic complex may be represented by Formula 1B, wherein in Formula 1B, $R_{1a}$ and $R_{1b}$ are each independently selected from a phenyl group, a naphthyl group, an anthryl group, a pyrenyl group, a phenanthrenyl group, a fluorenyl group, a pyridinyl group, a pyrazinyl group, a pyrimidinyl group, a triazinyl group, a quinolinyl group, an isoquinolinyl group, a quinoxalinyl group, a phenanthrolinyl group, and a carbazolyl group, and $R_{1a}$ and $R_{1b}$ are bound to each other via a single bond, and $R_2$ is selected from:

i) F, a cyano group, and a nitro group; and ii) a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, a tert-decanyl group, a phenyl group, a naphthyl group, an anthryl group, a pyrenyl group, a phenanthrenyl group, and a fluorenyl group, each substituted with at least one of F or a $C_1$-$C_{10}$ alkyl group.

The organometallic complex may be one of Complexes 1 to 18 below, but is not limited thereto:

1

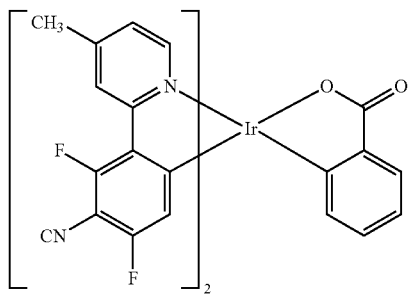

2

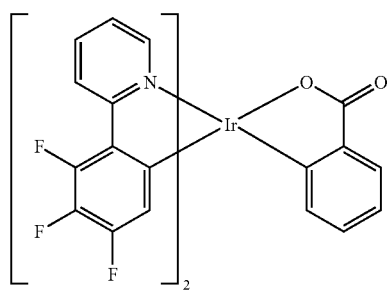

3

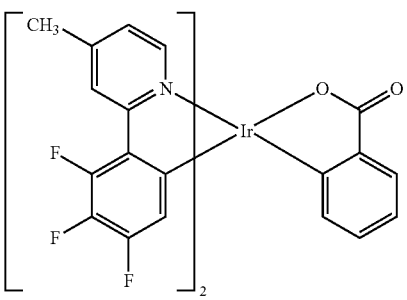

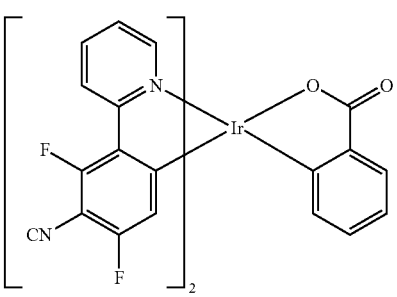

4

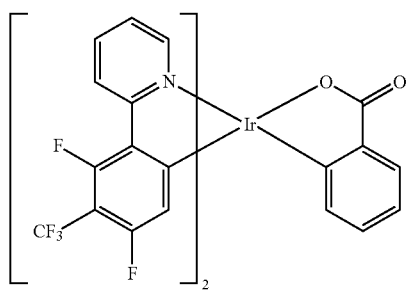

5

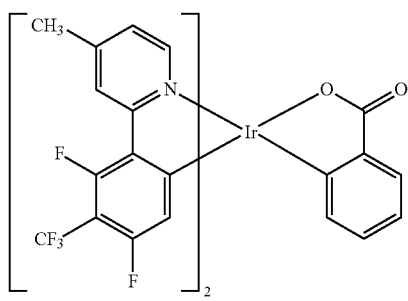

6

7

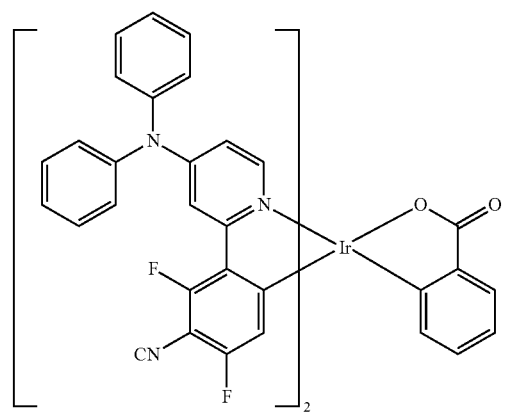

8

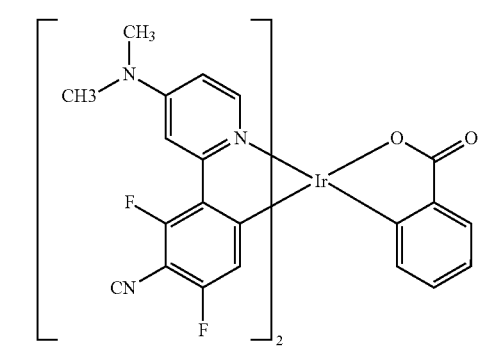

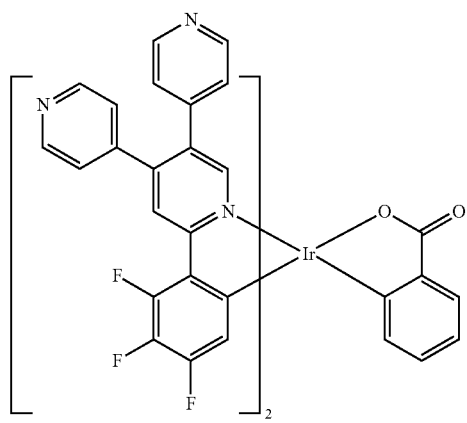
9
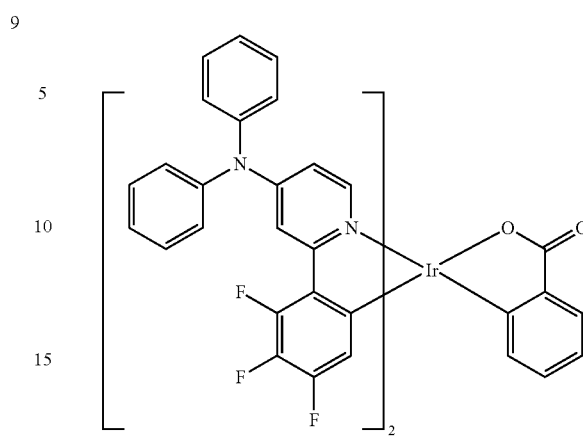
13
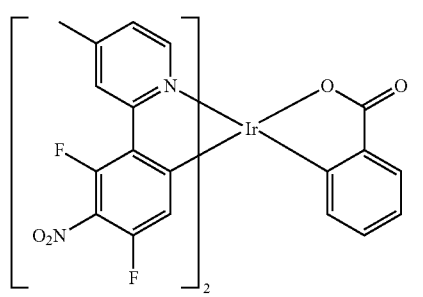
10
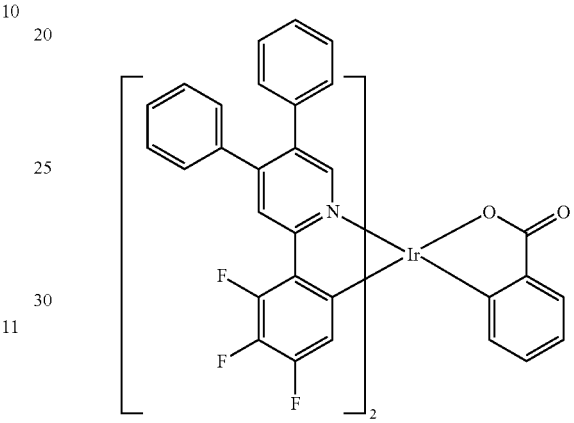
14
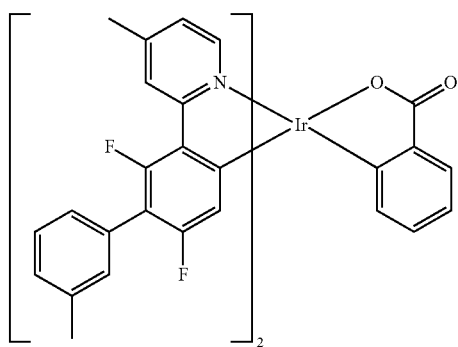
11
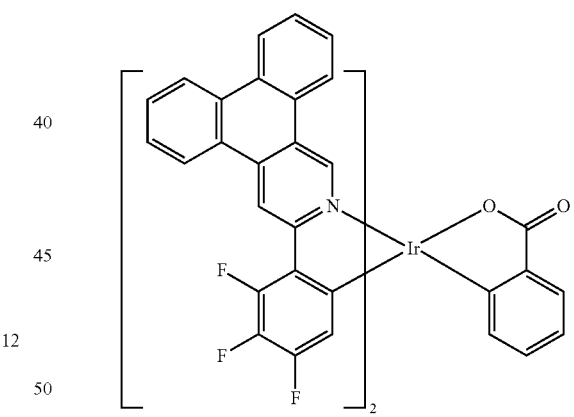
15
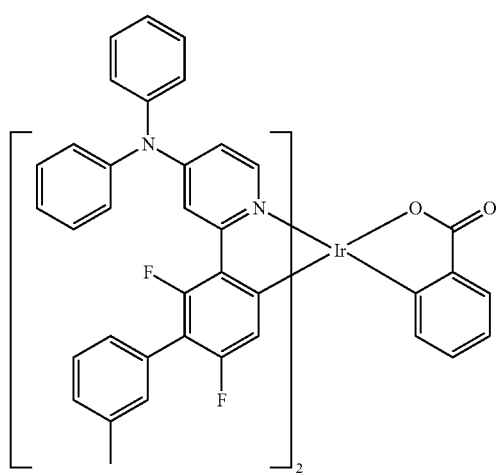
12
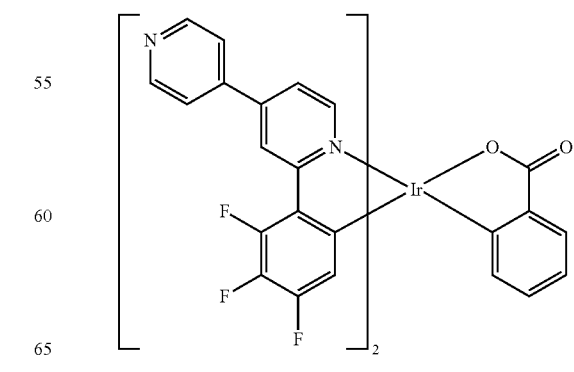
16

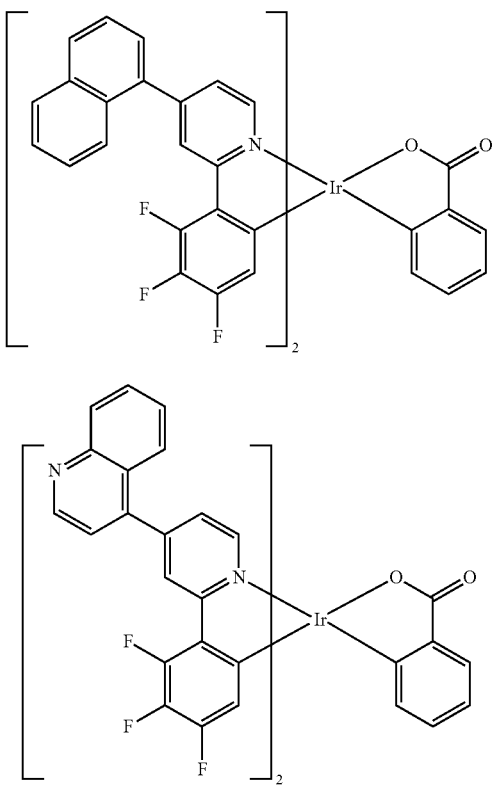

The organometallic complex includes a first fluorine and a second fluorine, which are an electron withdrawing group, as illustrated in Formula 1' below, and accordingly, an electron density of a benzene ring comprising the first fluorine and the second fluorine decreases. As a result, light emitted by the organometallic complex may be light that is shifted toward a shorter wavelength, for example, a blue light region. Also, since a ligand of the organometallic complex easily traps electrons, many excited excitons may be formed together with holes injected into an emission layer including the organometallic complex. Thus, an organic light-emitting diode (OLED) including the organometallic complex may have high luminescent efficiency.

Also, since the organometallic complex includes an auxiliary ligand as illustrated in Formula 1' below, a synthetic yield of the organometallic complex may increase. Since the organometallic complex includes an auxiliary ligand as illustrated in Formula 1' below, a detailed color wavelength can be adjusted and a molecular size of the organometallic complex can be controlled. Therefore, the possibility of receiving the exciton energy efficiently from the host in the emission layer increases. Thus, an OLED including the organometallic complex may have high luminescent efficiency.

Furthermore, when $R_2$ in Formula 1' below is an electron withdrawing group, an electron density of a benzene comprising $R_2$ decreases. As a result, light emitted by the organometallic complex may be light that is shifted toward a shorter wavelength, for example, a blue region. Also, since a ligand of the organometallic complex easily traps electrons, many excited excitons may be formed together with holes injected into an emission layer including the organometallic complex. Thus, an OLED including the organometallic complex may have high luminescent efficiency.

Accordingly, the organometallic complex represented by Formula 1 may emit various colors of light, which are tuned in detail, with a high luminescent efficiency.

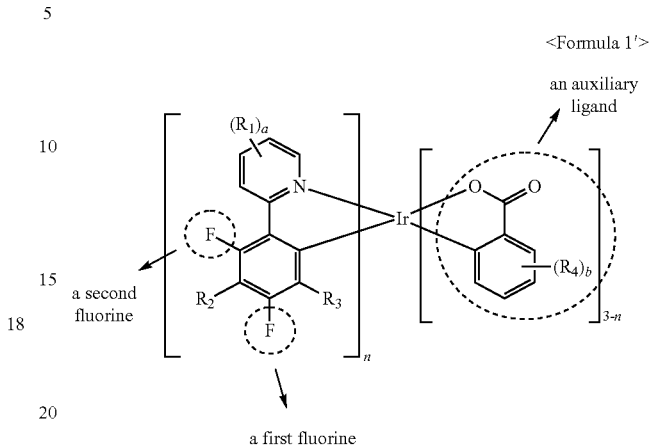

<Formula 1'>

The organometallic complex of Formula 1 may be synthesized by using a known organic synthesis method. The organometallic complex synthesis method may be obvious to one of ordinary skill in the art by referring to examples to be described later.

At least one of the organometallic complexes of Formula 1 may be used between a pair of electrodes of an OLED. For example, at least one of the organometallic complexes may be used in an emission layer.

Accordingly, an OLED including a first electrode, a second electrode disposed opposite to the first electrode, and an organic layer that is interposed between the first electrode and the second electrode and includes an emission layer, wherein the organic layer includes at least one of the organometallic complexes of Formula 1.

The wording that "an (organic layer) includes at least one of the organometallic complexes" used herein means that "an (organic layer) may include one kind of the organometallic complexes of Formula 1, or two or more different kinds of the organometallic complexes of Formula 1."

For example, the organic layer includes only Complex 1 as the organometallic complex. In this regard, Complex 1 may be present in the emission layer of the OLED. According to another embodiment, the organic layer includes Complexes 1 and 2 as the organometallic complex. In this regard, Complexes 1 and 2 may be present in the identical layer (i.e., the emission layer).

The organic layer may include, i) a hole transportation region between the first electrode and the emission layer, comprising at least one layer selected from a hole injection layer, a hole transport layer, a functional layer having both hole injection and hole transport capabilities (hereinafter referred to as a "H-functional layer"), a buffer layer, and an electron blocking layer, and ii) an electron transportation region between the emission layer and the second electrode, comprising at least one layer selected from a hole blocking layer, an electron transport layer, and an electron injection layer.

The term "organic layer" used herein refers to a single layer and/or a multi layer interposed between the first and the second electrodes of the OLED.

The organic layer includes an emission layer, and the emission layer may include at least one of the organometallic complexes described above.

The organometallic complex included in the emission layer may act as a phosphorescent dopant, and the emission layer may further include a host. Examples of the host will be described later.

As described above, an OLED including the organometallic complex may emit phosphorescent light within a green light area to a blue light area.

FIG. 1 illustrates a cross-sectional view of the structure of an OLED 10 according to an embodiment. Hereinafter, the structure and manufacturing method of an OLED according to an embodiment is described in detail with reference to FIG. 1.

A substrate 11, which may be any substrate that is used in a general OLED, may be a glass substrate or a transparent plastic substrate with excellent mechanical strength, thermal stability, transparency, surface smoothness, ease of handling, and water resistance.

A first electrode 13 may be formed by, for example, depositing or sputtering a material for a first electrode on the substrate 11. When the first electrode 13 is an anode, the material for the first electrode may be selected from materials with a high work function to enable ease of hole injection. The first electrode 13 may be a reflective electrode or a transmission electrode. The material for the first electrode may be a transparent material with high conductivity, and examples of such a material are indium tin oxide (ITO), indium zinc oxide (IZO), tin oxide (SnO2), and zinc oxide (ZnO). When magnesium (Mg), aluminum (Al), aluminum-lithium (Al—Li), calcium (Ca), magnesium-indium (Mg—In), magnesium-silver (Mg—Ag), or the like is used, the first electrode 13 may be used as a reflective electrode.

The first electrode 13 may have a single-layer structure or a multi-layer structure including at least two layers. For example, the first electrode 13 may have a three-layered structure of ITO/Ag/ITO, but is not limited thereto.

The organic layer 15 may be disposed on the first electrode 13.

An organic layer 15 may include a hole injection layer, a hole transport layer, a buffer layer, an emission layer, an electron transport layer, and an electron injection layer.

A hole injection layer (HIL) may be formed on the first electrode 13 by using various methods, such as vacuum deposition, spin coating, casting, Langmuir-Blodgett (LB) deposition.

When the HIL is formed using vacuum deposition, vacuum deposition conditions may vary depending on the compound that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using spin coating, the coating conditions may vary depending on the compound that is used to form the HIL, and the desired structure and thermal properties of the HIL to be formed. For example, the coating rate may be in the range of about 2,000 rpm to about 5,000 rpm, and a temperature at which heat treatment is performed to remove a solvent after coating may be in the range from about 80° C. to about 200° C. However, the coating conditions are not limited thereto.

As a hole injection material, any known hole injection material may be used, and examples thereof are N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris(3-methylphenyl-phenylamino)triphenylamine (m-MTDATA), N,N'-di(1-naphthyl)-N,N'-diphenylbenzidine (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), or (polyaniline)/poly(4-styrenesulfonate) (Pani/PSS) may be used, but the hole injection material is not limited thereto:

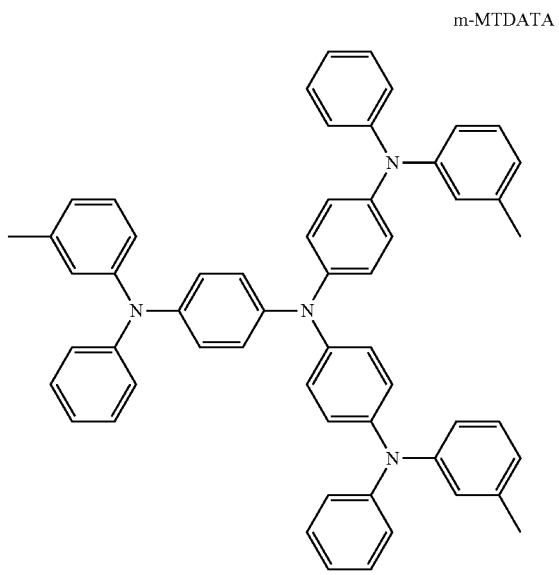

m-MTDATA

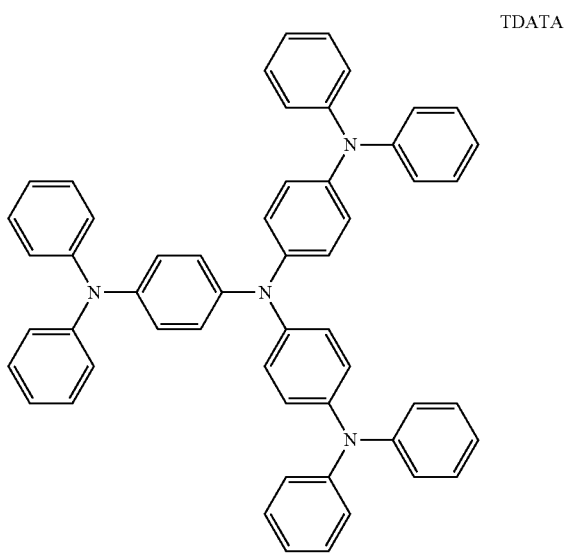

TDATA

2-TNATA

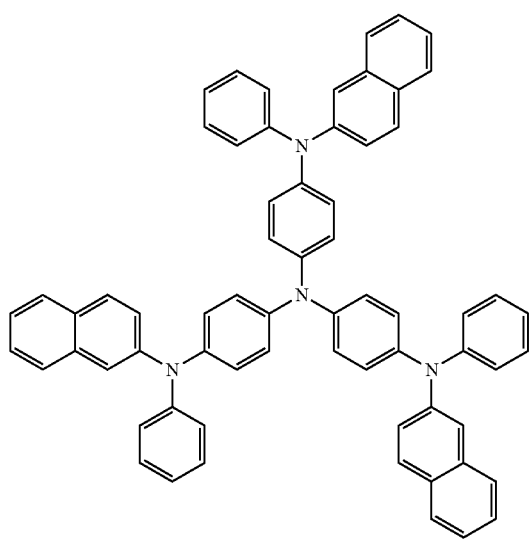

A thickness of the HIL may be in a range from about 100 Å to about 10,000 Å, for example, from about 100 Å to about 1,000 Å. When the thickness of the HIL is within these ranges, the HIL may have satisfactory hole injection characteristics without a substantial increase in a driving voltage.

Then, a hole transport layer (HTL) may be formed on the HIL by using vacuum deposition, spin coating, casting, LB deposition, or the like. When the HTL is formed using vacuum deposition or spin coating, the deposition and coating conditions may be similar to those for the formation of the HIL, though the deposition and coating conditions may vary depending a compound that is used to form the HTL.

As a hole transport material, any known hole transport material may be used, and examples thereof are a carbazole derivative such as N-phenylcarbazole or polyvinylcarbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), N,N'-di(1-naphthyl)-N,N'-diphenylbenzidine (NPB), or the like may be used, but the hole transport material is not limited thereto.

TPD

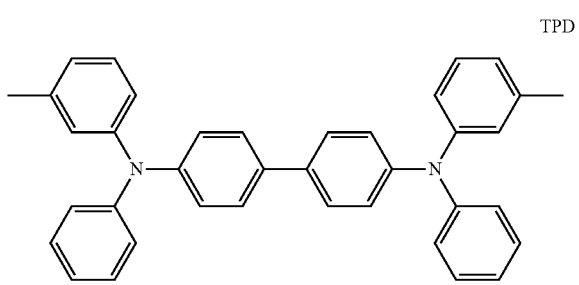

A thickness of the HTL may be in a range from about 50 Å to about 2,000 Å, for example, from about 100 Å to about 1,500 Å. When the thickness of the HTL is within these ranges, the HTL may have satisfactory hole transport characteristics without a substantial increase in a driving voltage.

The H-functional layer (a functional layer having a hole injection ability and a hole transport ability) may include one or more materials selected from the materials for the HIL and the materials for the HTL. A thickness of the H-functional layer may be in a range from about 100 Å to about 10,000 Å, for example, from about 100 Å to about 1,000 Å. When the thickness of the H-functional layer is within these ranges, the H-functional layer may have satisfactory hole injection and transport characteristics without a substantial increase in a driving voltage.

In addition, at least one layer of the hole injection layer, the hole transport layer, and the H-functional layer may include at least one of a compound represented by Formula 300 below and a compound represented by Formula 350 below:

<Formula 300>

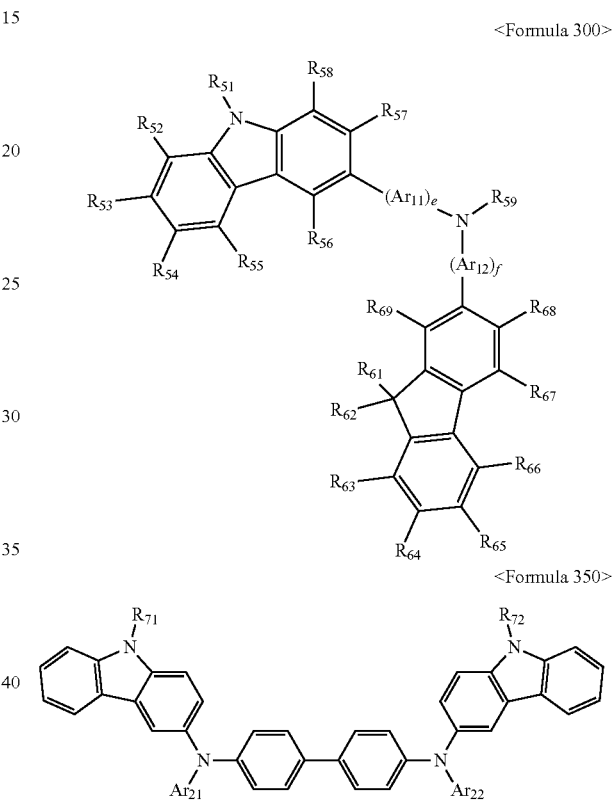

<Formula 350>

$Ar_{11}$ and $Ar_{12}$ in Formula 300 may be each independently a substituted or unsubstituted $C_6$-$C_{60}$ arylene group. For example, $Ar_{11}$ and $Ar_{12}$ are each independently a substituted or unsubstituted phenylene group, a substituted or unsubstituted naphthylene group, a substituted or unsubstituted fluorenylene group, or a substituted or unsubstituted anthrylene group, but is not limited thereto. At least one substituent of at least one of the substituted phenylene group, the substituted naphthylene group, the substituted fluorenylene group, and the substituted anthrylene group may be a deuterium atom, a halogen atom, a hydroxyl group, a cyano group, a $C_1$-$C_{20}$ alkyl group, a $C_1$-$C_{20}$ alkoxy group, a phenyl group, a naphthyl group, an anthryl group, a carbazolyl group, or a phenyl-substituted carbazolyl group, but is not limited thereto.

$Ar_{21}$ and $Ar_{22}$ in Formula 350 may be each independently a substituted or unsubstituted $C_6$-$C_{60}$ aryl group or a substituted or unsubstituted $C_2$-$C_{60}$ heteroaryl group. For example, $Ar_{21}$ and $Ar_{22}$ may be each independently a substituted or unsubstituted a phenyl group, a substituted or unsubstituted a naphthyl group, a substituted or unsubstituted phenanthrenyl group, a substituted or unsubstituted an anthryl group, a substituted or unsubstituted a pyrenyl group, a substituted or unsubstituted chrycenyl group, a substituted or unsubstituted a fluorenyl group, a substituted or unsubstituted a carbazolyl group, a substituted or unsubstituted dibenzofuranyl group, or a substituted or unsubstituted dibenzothiophenyl group. In this regard, at least one substituent of the substituted phenyl group, the substituted naphthyl group, the substituted phenanthrenyl group, the substituted anthryl group, the substituted pyrenyl group, the substituted chrycenyl group, the substituted fluorenyl group, the substituted carbazolyl group, the substituted dibenzofuranyl group, and the substituted dibenzothiophenyl group may be selected from:

a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, a phosphoric acid or a salt thereof, a $C_1$-$C_{10}$ alkyl group and a $C_1$-$C_{10}$ alkoxy group;

a phenyl group, a naphthyl group, a fluorenyl group, phenanthrenyl group, an anthryl group, a triphenylenyl group, a pyrenyl group, chrycenyl group, an imidazolyl group, an imidazolinyl group, an imidazopyridinyl group, an imidazopyrimidinyl group, a pyridinyl group, a pyrazinyl group, a pyrimidinyl group, and an indolyl group; and a phenyl group, a naphthyl group, a fluorenyl group, phenanthrenyl group, an anthryl group, a triphenylenyl group, a pyrenyl group, chrycenyl group, an imidazolyl group, an imidazolinyl group, an imidazopyridinyl group, an imidazopyrimidinyl group, a pyridinyl group, a pyrazinyl group, a pyrimidinyl group, and an indolyl group, each substituted with at least one of a deuterium atom a halogen atom, a hydroxyl group, a cyano group, a nitro group, an amino group, an amidino group, a hydrazine, a hydrazone, a carboxyl group or a salt thereof, a sulfonic acid or a salt thereof, a phosphoric acid or a salt thereof, a $C_1$-$C_{10}$ alkyl group, and a $C_1$-$C_{10}$ alkoxy group.

e and f in Formula 300 may be each independently an integer from 0 to 5, or may be 0, 1, or 2. For example, e may be 1 and f may be 0, but e and f are not limited thereto.

$R_{51}$ to $R_{58}$, $R_{61}$ to $R_{69}$, and $R_{71}$ and $R_{72}$ in Formulae 300 and 350 are each independently a hydrogen atom, a deuterium atom, a halogen atom, a hydroxyl group, a cyano group, —$NO_2$, an amino group, an amidino group, a hydrazine, a hydrazone, a carboxyl group or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, or a substituted or unsubstituted $C_6$-$C_{60}$ arylthio group.

For example, $R_{51}$ to $R_{58}$, $R_{61}$ to $R_{69}$ and $R_{71}$ and $R_{72}$ may be each independently selected from:

a hydrogen atom, a deuterium atom, a halogen atom, a hydroxyl group, a cyano group, —$NO_2$, an amino group, an amidino group, a hydrazine, a hydrazone, a carboxyl group or a salt thereof, a sulfonic acid or a salt thereof, a phosphoric acid or a salt thereof, a $C_1$-$C_{10}$ alkyl group (i.e., a methyl group, an ethyl group, a propyl group, a butyl group, a pentyl group, a hexyl group, or the like) and a $C_1$-$C_{10}$ alkoxy group (i.e., a methoxy group, an ethoxy group, a propoxy group, a butoxy group, a pentoxy group, or the like);

a $C_1$-$C_{10}$ alkyl group and a $C_1$-$C_{10}$ alkoxy group, each substituted with at least one of a deuterium atom, a halogen atom, a hydroxyl group, a cyano group, —$NO_2$, an amino group, an amidino group, a hydrazine, a hydrazone, a carboxyl group or a salt thereof, a sulfonic acid or a salt thereof, and a phosphoric acid or a salt thereof;

a phenyl group, a naphthyl group, an anthryl group, a fluorenyl group and a pyrenyl group; and a phenyl group, a naphthyl group, an anthryl group, a fluorenyl group, and a pyrenyl group, each substituted with at least one of a deuterium atom, a halogen atom, a hydroxyl group, a cyano group, —$NO_2$, an amino group, an amidino group, a hydrazine, a hydrazone, a carboxyl group or a salt thereof, a sulfonic acid or a salt thereof, a phosphoric acid or a salt thereof, a $C_1$-$C_{10}$ alkyl group, and a $C_1$-$C_{10}$ alkoxy group, but is not limited thereto.

$R_{59}$ in Formula 300 may be selected from:

a phenyl group, a naphthyl group, an anthryl group, a biphenyl group and a pyridyl group; and a phenyl group, a naphthyl group, an anthryl group, a biphenyl group, and a pyridyl group, each substituted with at least one of a deuterium atom, a halogen atom, a hydroxyl group, a cyano group, —$NO_2$, an amino group, an amidino group, a hydrazine, a hydrazone, a carboxyl group or a salt thereof, a sulfonic acid or a salt thereof, a phosphoric acid or a salt thereof, a substituted or unsubstituted $C_1$-$C_{20}$ alkyl group, and a substituted or unsubstituted $C_1$-$C_{20}$ alkoxy group.

According to an embodiment, the compound represented by Formula 300 may also be represented by Formula 300A below, but is not limited thereto:

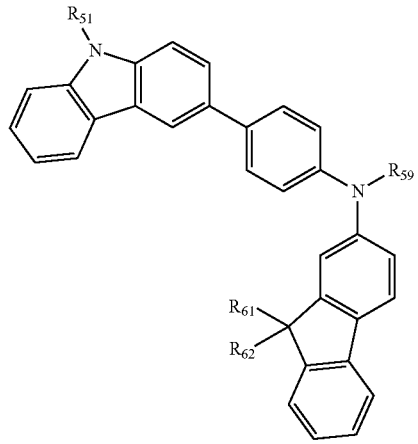

<Formula 300A>

$R_{51}$, $R_{61}$, $R_{62}$, and $R_{59}$ in Formula 300A are already described above.

For example, at least one layer selected from the hole injection layer, the hole transport layer, and the H-functional layer may include at least one of Compounds 301 to 320, but is not limited thereto:

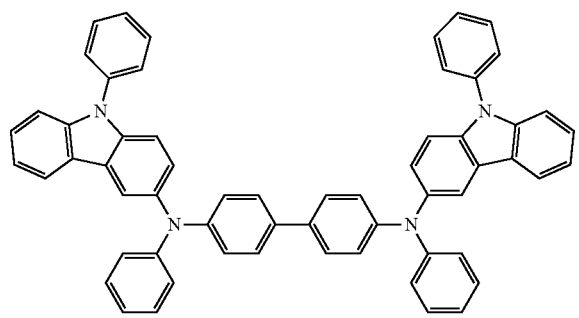
301
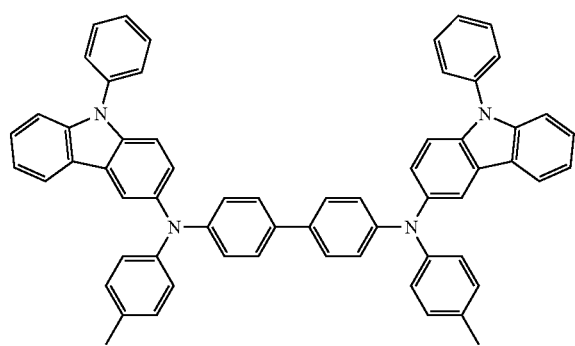
302
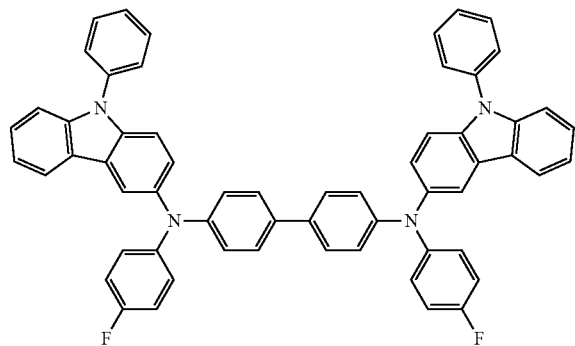
303
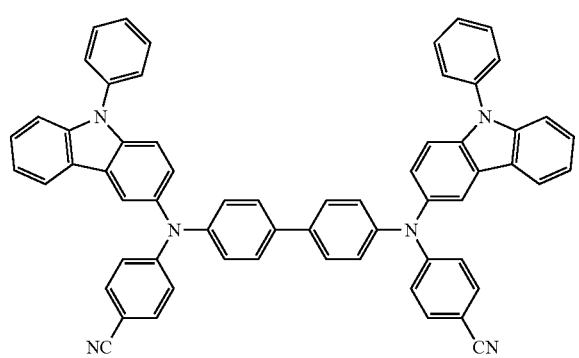
304
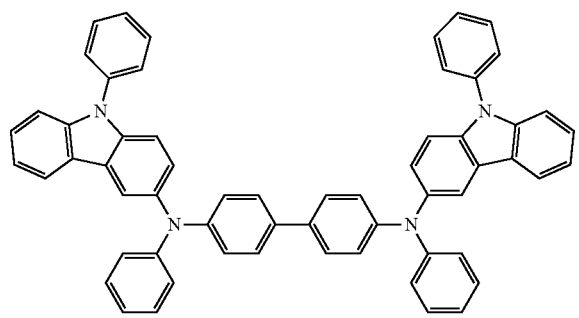
305
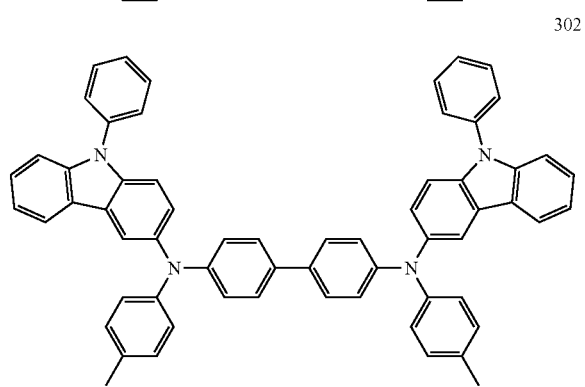
306
307
308

309
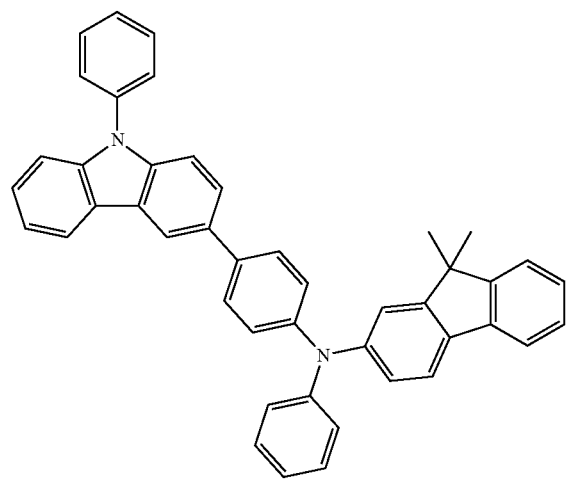
310
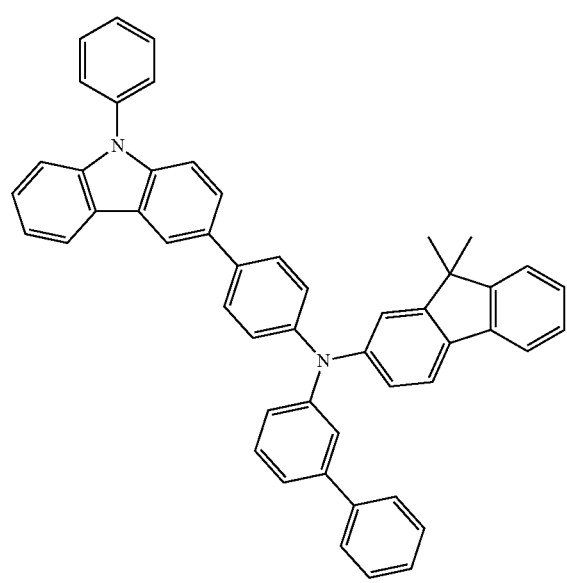
311
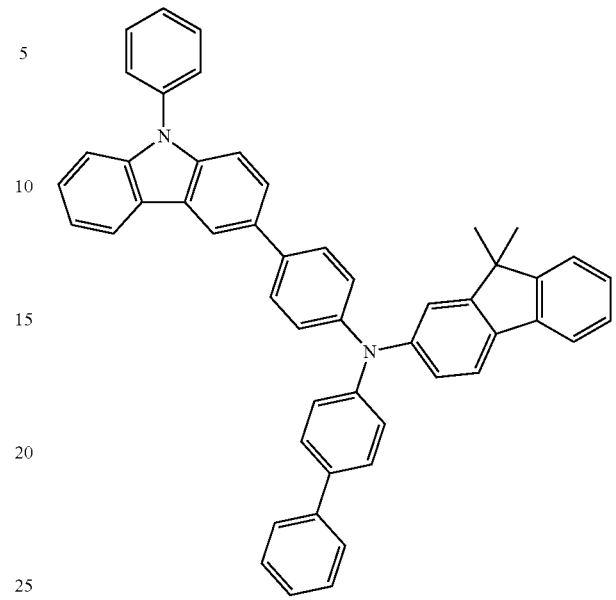
312
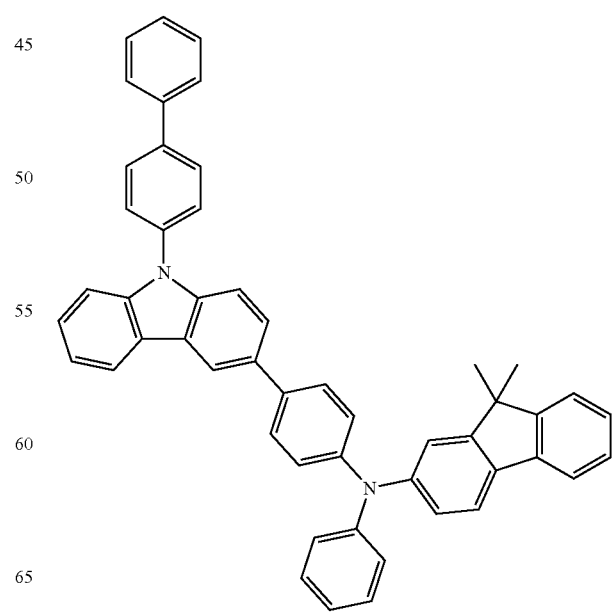

313
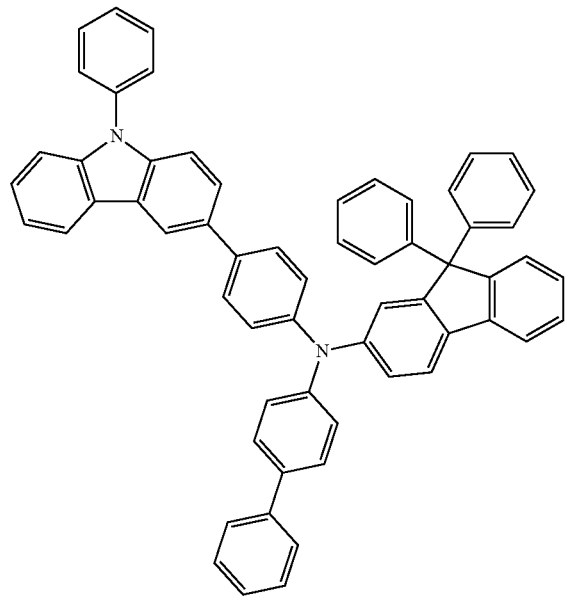
314
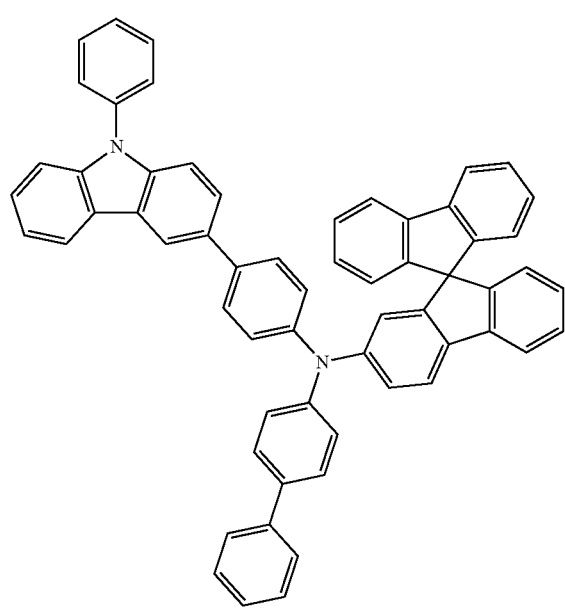
315
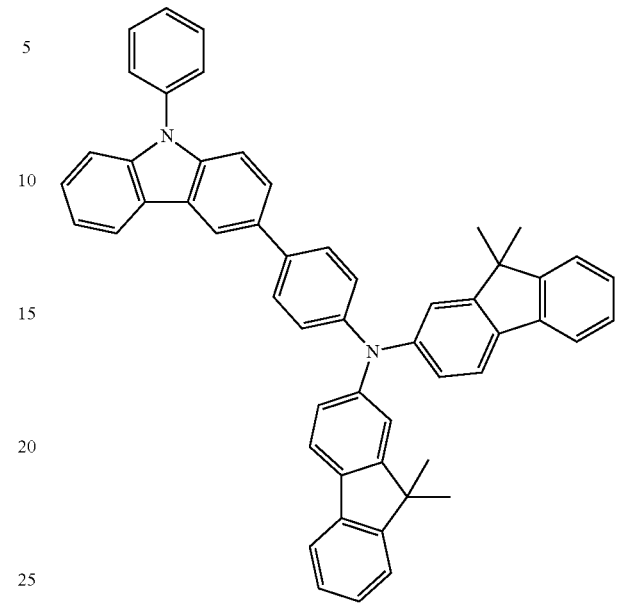
316
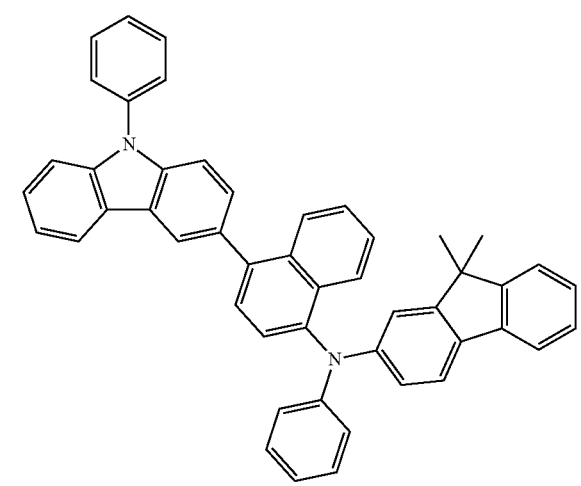

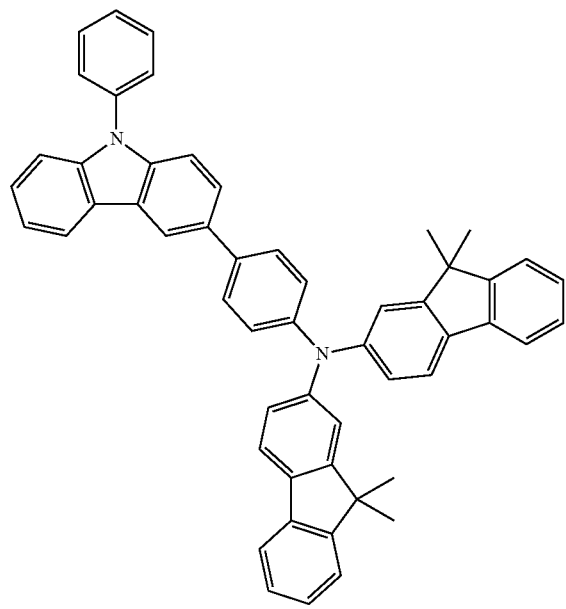

317

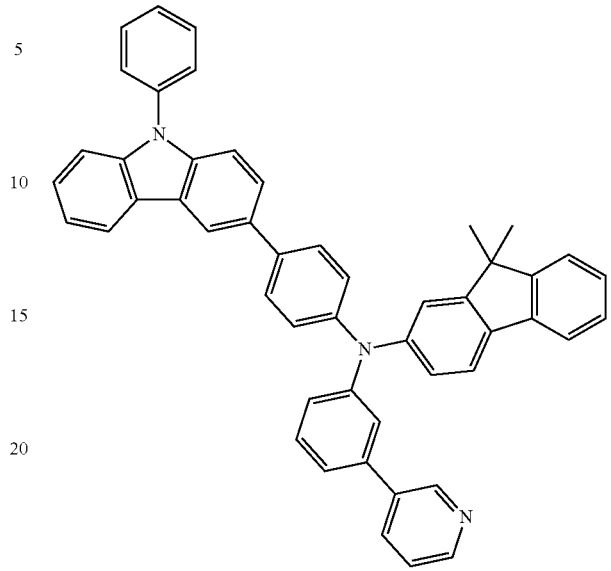

319

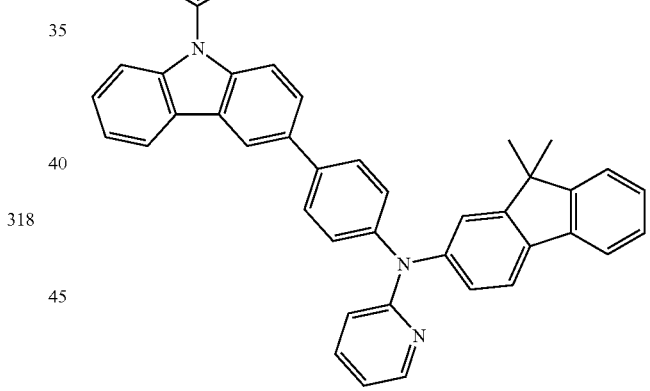

320

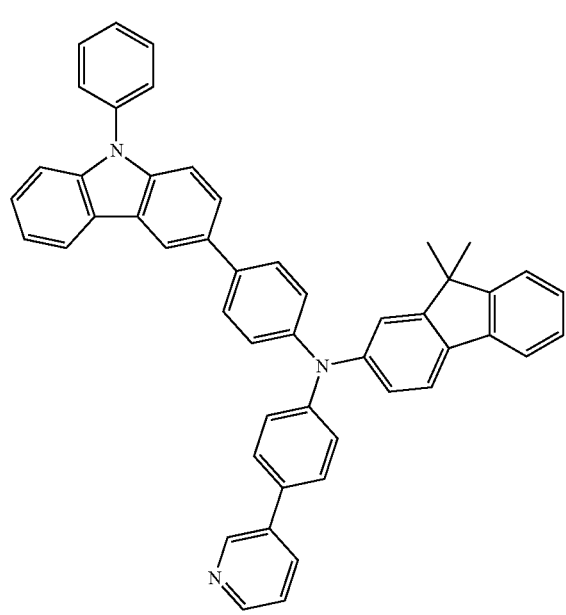

318

At least one of the hole injection layer, the hole transport layer, and the H-functional layer may further include a charge-generating material to improve layer conductivity, in addition to a known hole injection material, a known hole transport material, and/or material having both hole injection and hole transport capabilities as described above.

The charge-generating material may be, for example, a p-dopant. The p-dopant may be one of quinine derivatives, metal oxides, and compounds with a cyano group, but are not limited thereto. For example, non-limiting examples of the p-dopant are quinine derivatives, such as tetracyanoquinodimethane (TCNQ) and 2,3,5,6-tetrafluoro-tetracyano-1,4-benzoquinodimethane (F4-TCNQ); metal oxide such as tungsten oxide and molybdenym oxide; and a cyano group-containing compound such as Compound 200 below, but is not limited thereto.

<Compound 200>

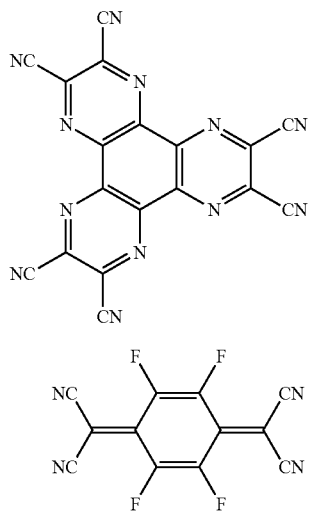

<F4-TCNQ> mCP

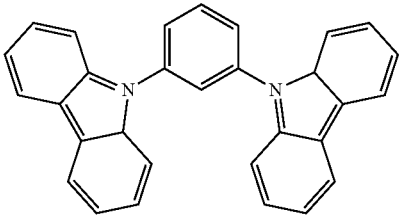

OXD-7

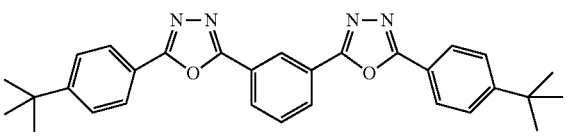

When the hole injection layer, hole transport layer, or H-functional layer further includes a charge-generating material, the charge-generating material may be homogeneously dispersed or non-homogeneously distributed in the layer.

A buffer layer may be disposed between at least one of the HIL, the HTL, and the H-functional layer, and the emission layer. The buffer layer may compensate for an optical resonance distance of light according to a wavelength of the light emitted from the emission layer, and thus may increase efficiency. The butter layer may include any hole injecting material or hole transporting material that are widely known. In some other embodiments, the buffer layer may include the same material as one of the materials included in the HIL, HTL, and H-functional layer that underlie the buffer layer.

Then, an emission layer (EML) may be formed on the HTL, the H-functional layer, or the buffer layer by vacuum deposition, spin coating, casting, LB deposition, or the like. When the EML is formed using vacuum deposition or spin coating, the deposition and coating conditions may be similar to those for the formation of the HIL, though the conditions for deposition and coating may vary depending on the material that is used to form the EML.

The EML may include at least one of the organometallic complexes.

The organometallic complex included in the EML may act as a dopant (i.e., a blue phosphorescent dopant). In this regard, the EML may further include, in addition to the organometallic complex, a host.

The host may be at least one of known hosts. As the host, Alq3, 4,4'-N,N'-dicarbazol-biphenyl (CBP), poly(n-vinyl-carbazole) (PVK), 9,10-di(naphthalen-2-yl)anthracene (ADN), TCTA, 1,3,5-tris(N-phenylbenzimidazole2-yl)benzene (TPBI), 3-tert-butyl-9,10-di(naphth-2-yl)anthracene (TBADN), mCP, or OXD-7 may be used, but the host is not limited thereto.

PVK

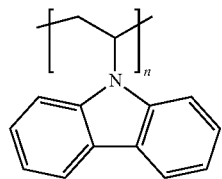

In some embodiments, a carbazole-based compound represented by Formula 10 below may be used as a host.

<Formula 10>

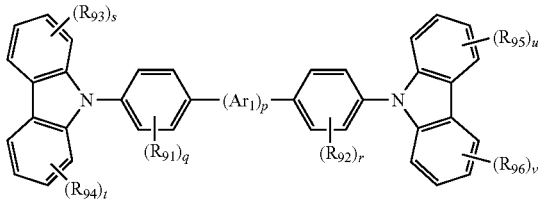

In Formula 10, Ar1 may be selected from a substituted or unsubstituted $C_1$-$C_{60}$ alkylene group, a substituted or unsubstituted $C_2$-$C_{60}$ alkenylene group, —C(=O)—, —N($R_{100}$)— (wherein $R_{100}$ is a substituted or unsubstituted $C_6$-$C_{60}$ aryl group, or a substituted or unsubstituted $C_2$-$C_{60}$ heteroaryl group), a substituted or unsubstituted $C_6$-$C_{60}$ arylene group, and a substituted or unsubstituted $C_2$-$C_{60}$ heteroarylene group;

p is an integer from 0 to 10

$R_{91}$ to $R_{96}$ are each independently selected from a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group, and two neighboring substituents of $R_{91}$ to $R_{96}$ are optionally bound to each other to form a substituted or unsubstituted $C_4$-$C_{20}$ alicyclic, a substituted or unsubstituted $C_2$-$C_{20}$ hetero alicyclic group, a substituted or unsubstituted $C_6$-$C_{20}$ aromatic ring, or a substituted or unsubstituted $C_2$-$C_{20}$ heteroaromatic ring;

and q, r, s, t, u, and v may be each independently an integer from 1 to 4.

Ar1 in Formula 10 may be a $C_1$-$C_5$ alkylene group, a $C_2$-$C_5$ alkenylene group, —C(=O)—, or —N($R_{100}$)—, wherein $R_{100}$ may be selected from:

a phenyl group, a naphthyl group, an anthryl group, a fluorenyl group, a carbazolyl group, a pyridinyl group, a pyrimidinyl group, and a triazinyl group; and a phenyl group, a naphthyl group, an anthryl group, a fluorenyl group, a carbazolyl group, a pyridinyl group, a pyrimidinyl group, and a triazinyl group, each substituted with at least one of a deuterium atom, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group.

$R_{91}$ to $R_{96}$ in Formula 10 may be each independently selected from:

a hydrogen atom, a deuterium atom, a halogen atom, a hydroxyl group, a cyano group, a nitro group, an amino group, an amidino group, a hydrazine, a hydrazone, a carboxyl group or a salt thereof, a sulfonic acid or a salt thereof, a phosphoric acid or a salt thereof, a $C_1$-$C_{20}$ alkyl group, and a $C_1$-$C_{20}$ alkoxy group; and a $C_1$-$C_{20}$ alkyl group and a $C_1$-$C_{20}$ alkoxy group, each substituted with at least one of a deuterium atom, a halogen atom, a hydroxyl group, a cyano group, a nitro group, and an amino group.

The carbazole-based compound may be one of the following compounds, but is not limited thereto:

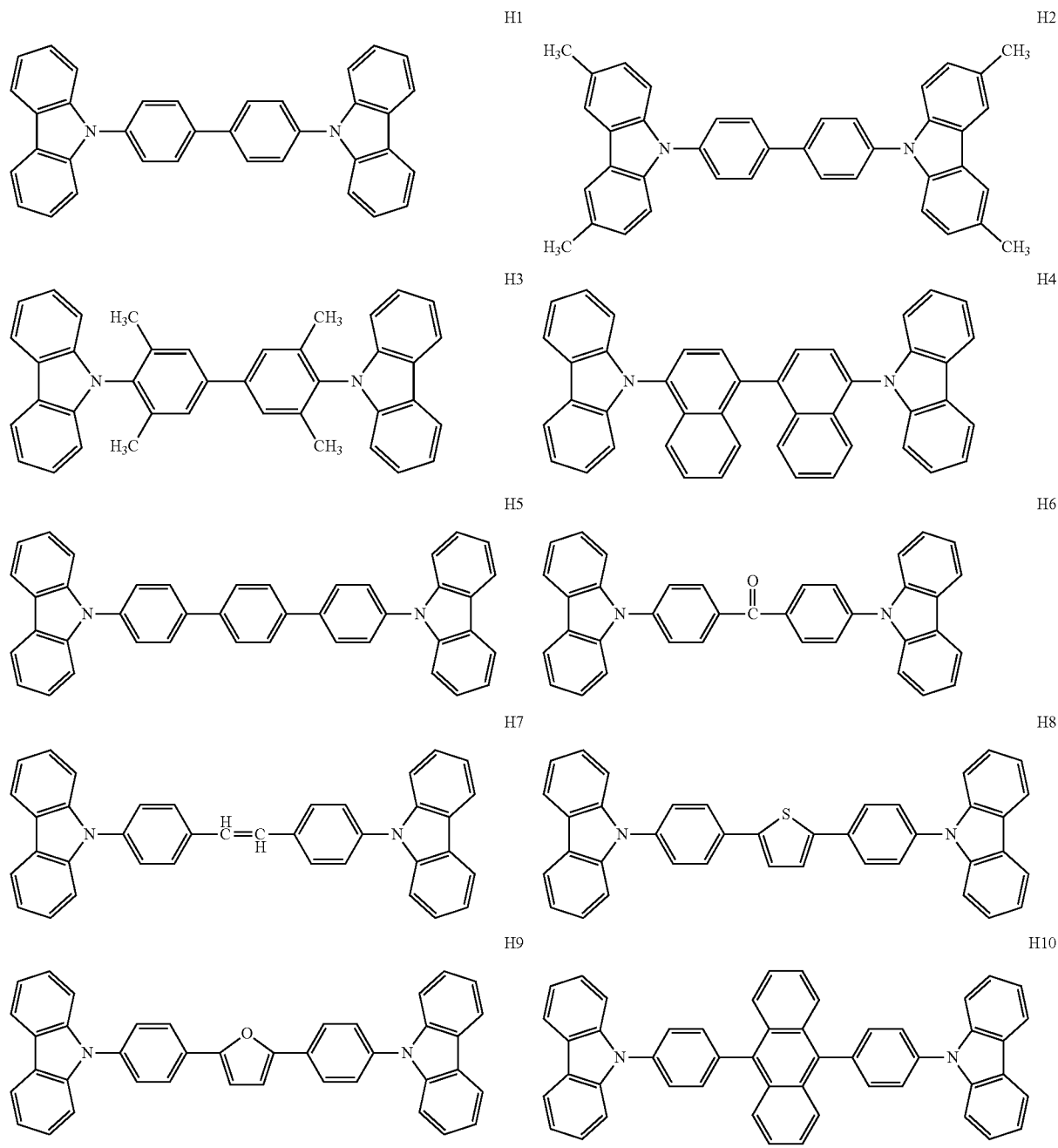

-continued
H11
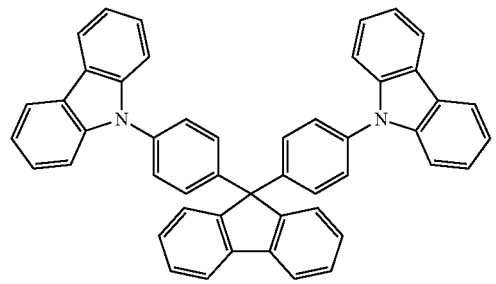
H12
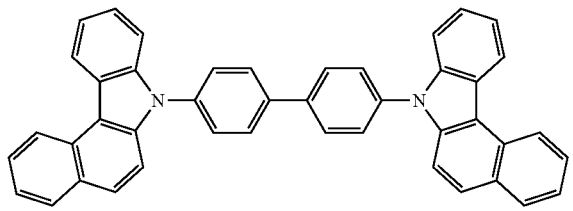
H13
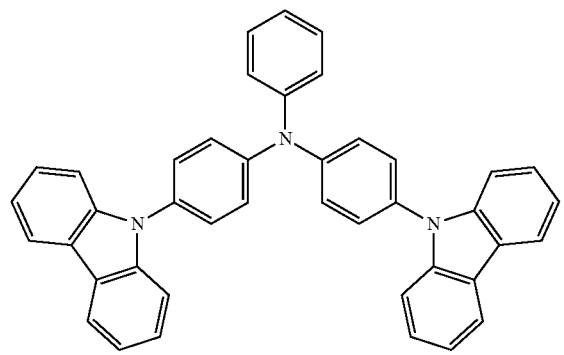
H14
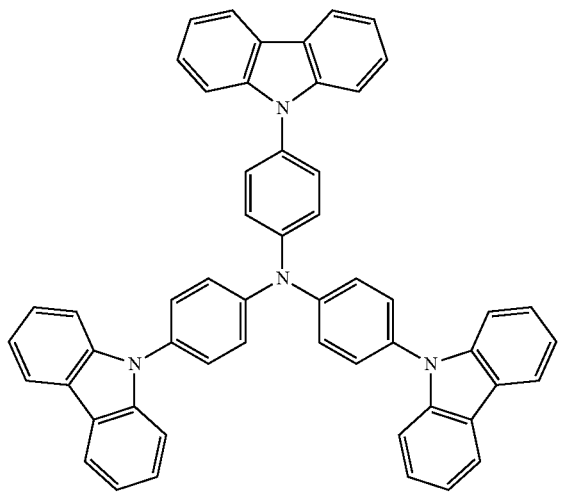
H15
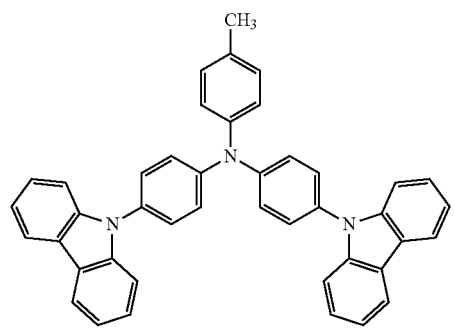
H16
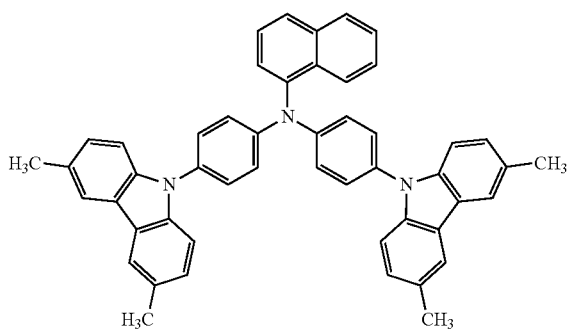
H17
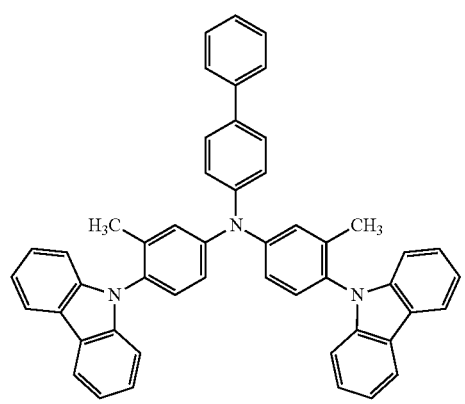
H18
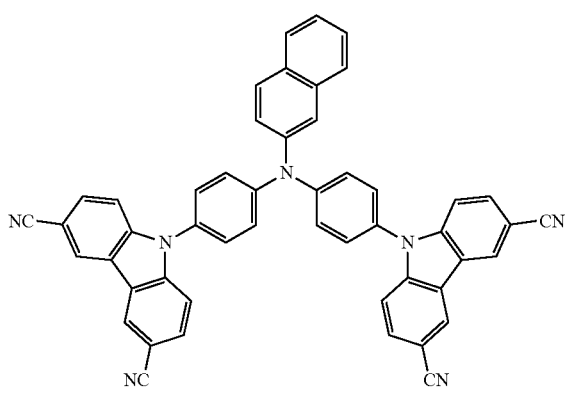

H19
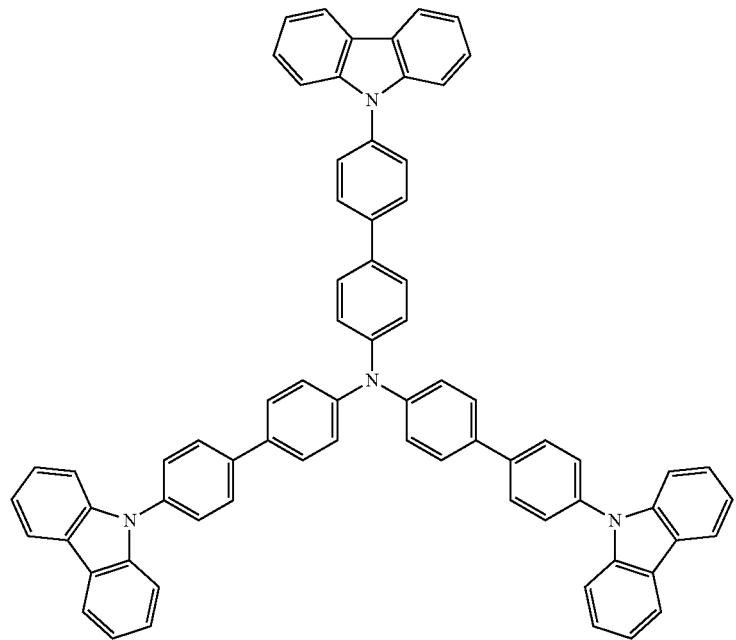
H20
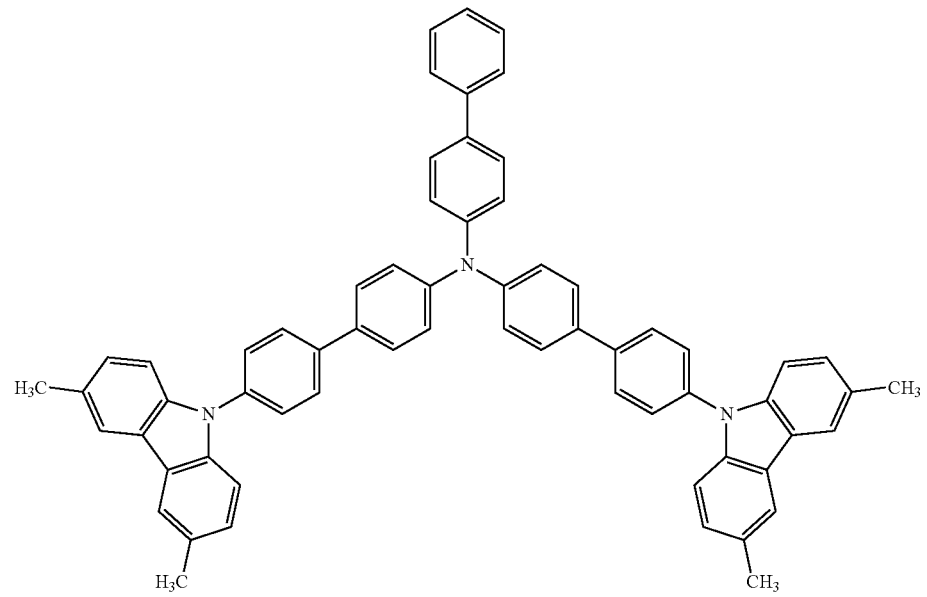

H21
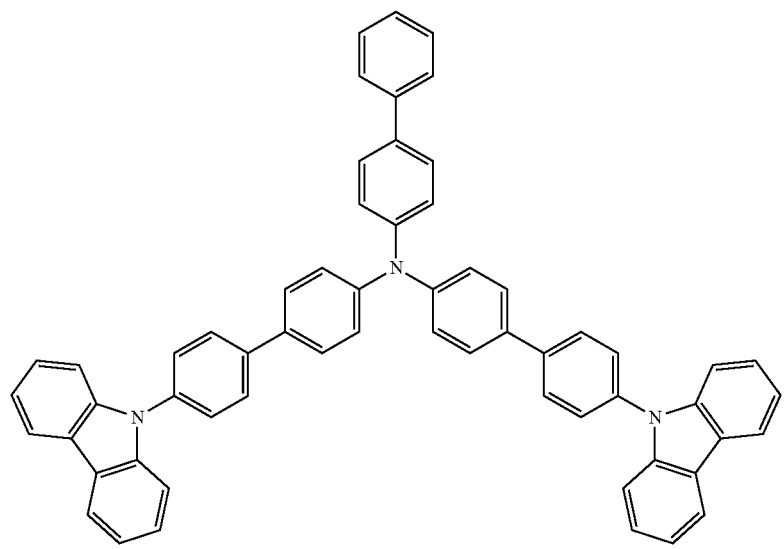
H22
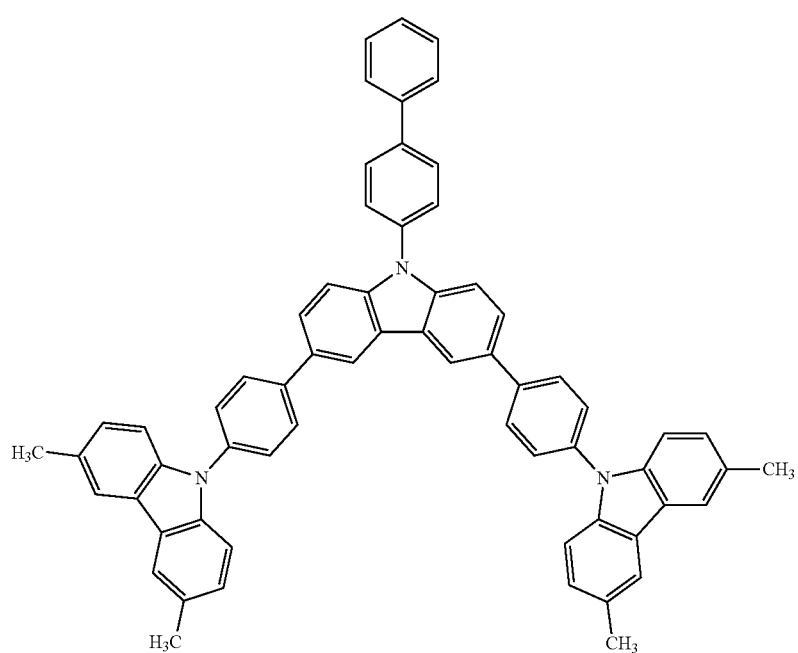
H23
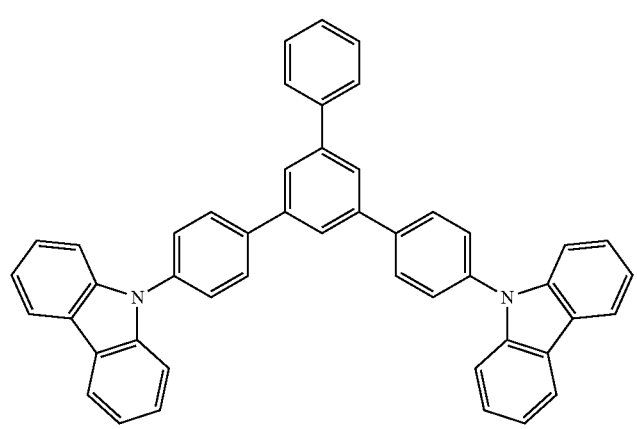

-continued
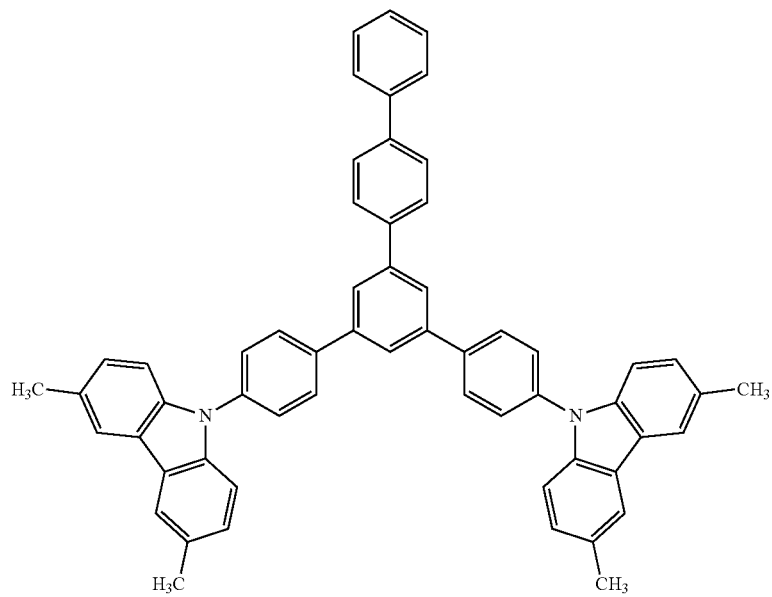
H24
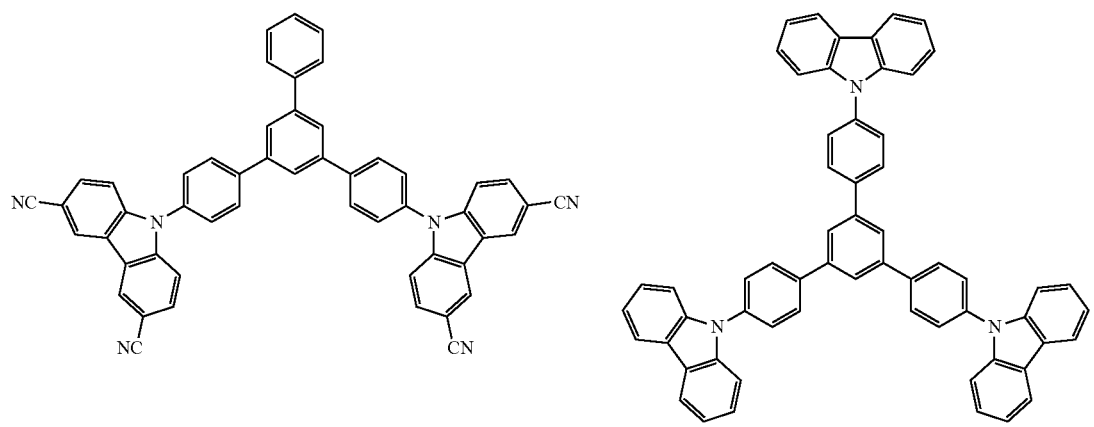
H25
H26
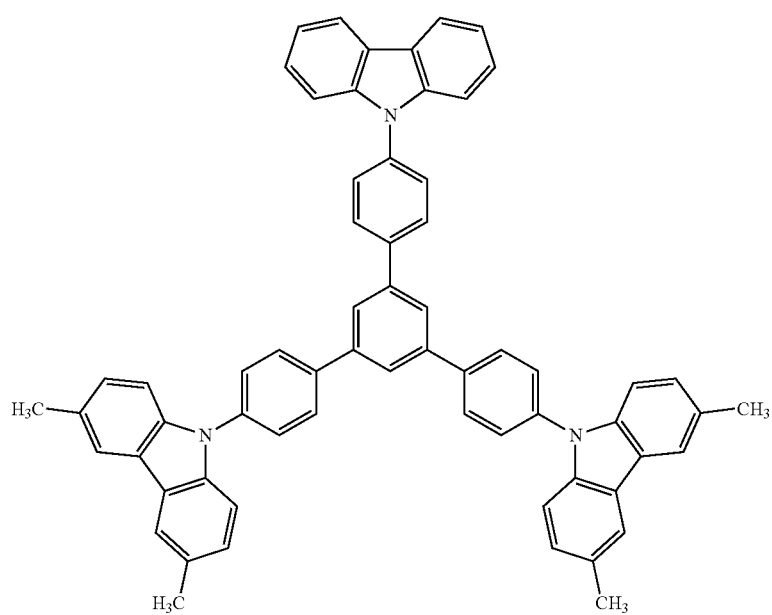
H27

-continued

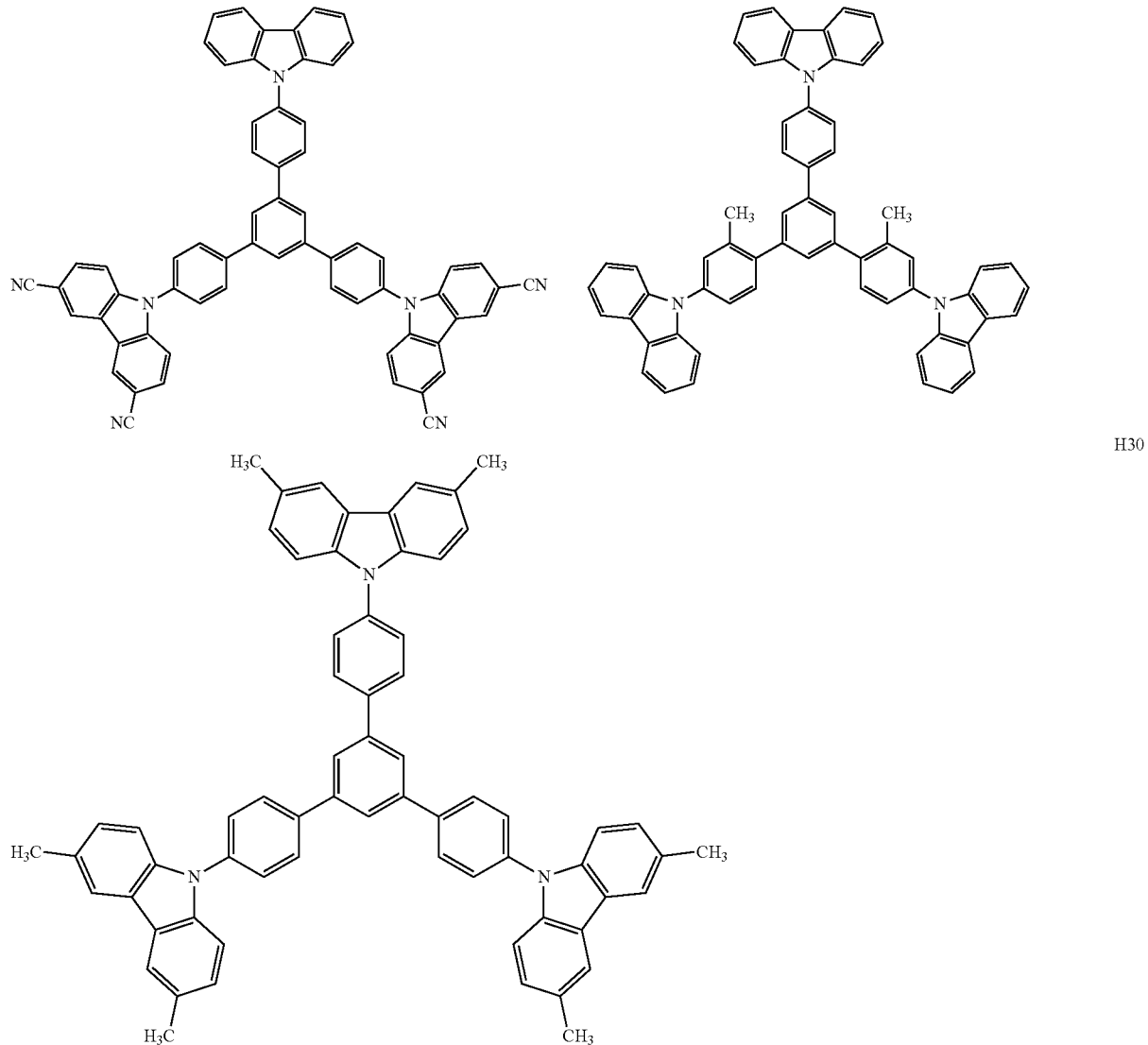

H28

H29

H30

When the emission layer includes a host and a dopant (that is, the organometallic complex represented by Formula 1), an amount of the dopant may be in a range from about 0.01 to about 15 wt %, based on 100 wt % of the emission layer, but is not limited thereto.

A thickness of the emission layer may be in a range of about 200 Å to about 700 Å. When the thickness of the EML is within these ranges, the EML may have improved light emitting ability without a substantial increase in driving voltage.

Next, an electron transport layer (ETL) is formed on the EML using various methods, for example, by vacuum deposition, spin coating, casting, or the like. When the ETL is formed using vacuum deposition or spin coating, the deposition and coating conditions may be similar to those for the formation of the HIL, though the conditions for deposition and coating may vary depending on the material that is used to form the ETL. As a material for an electron transport layer, known electron transportation materials that stably transport electrons injected from an electron injection electrode (cathode) may be used. Examples of known electron transportation materials are quinolin derivatives, in particular, tris(8-quinolate)aluminum ($Alq_3$), TAZ, Balq, beryllium bis(benzoquinolin-10-olate) (Bebq2), ADN, compound 101, compound 102, and Bphen, but are not limited thereto.

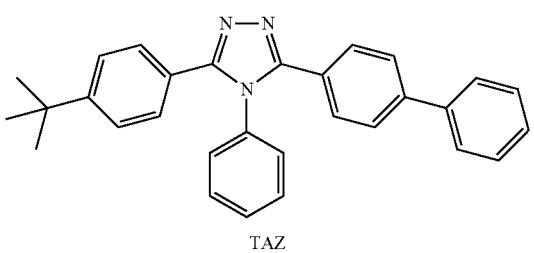

TAZ

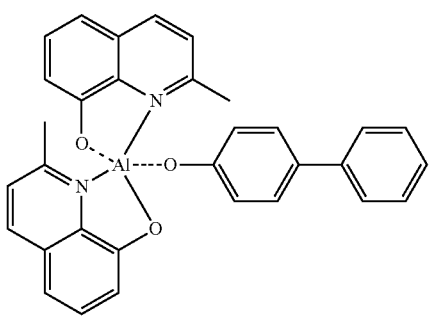

BAlq

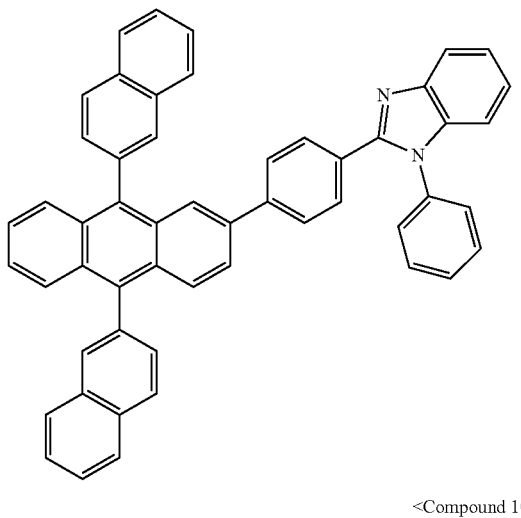

<Compound 101>

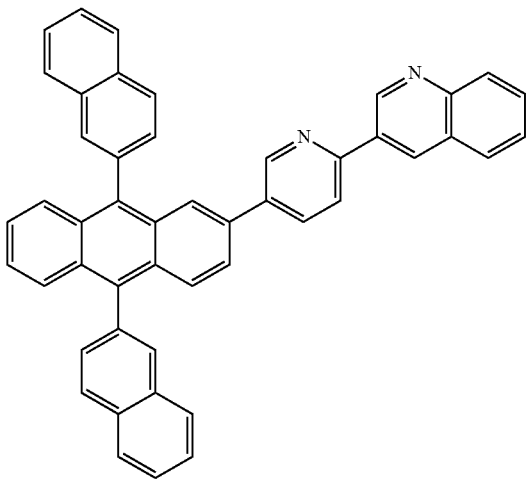

<Compound 102>

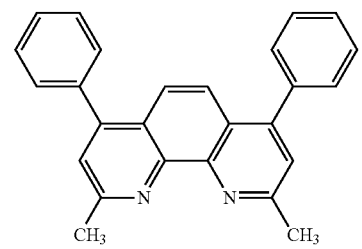

BCP

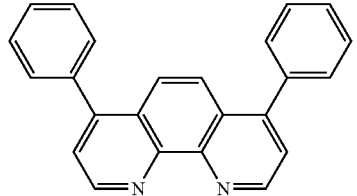

Bphen

A thickness of the ETL may be in a range of about 100 Å to about 1,000 Å, for example, from about 150 Å to about 500 Å. When the thickness of the ETL is within these ranges, the ETL may have satisfactory electron transporting ability without a substantial increase in driving voltage.

The ETL may further include, in addition to known electron transporting organic compounds, a metal-containing material.

The metal-containing material may include a lithium (Li) complex. Non-limiting examples of the Li complex are lithium quinolate (Liq) and Compound 203 below:

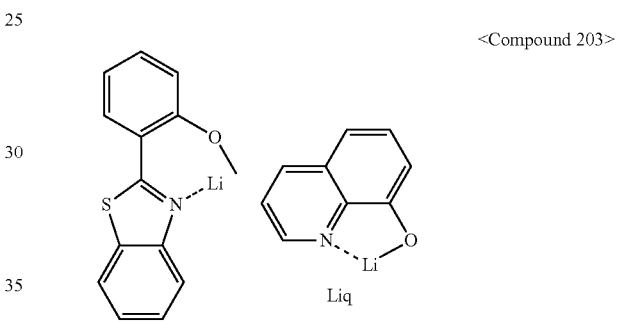

<Compound 203>

Liq

Then, an EIL, which facilitates injection of electrons from the second electrode may be formed on the ETL. Any suitable electron-injecting material may be used to form the EIL.

Examples of materials for forming the EIL are LiF, NaCl, CsF, $Li_2O$, and BaO, which are known in the art. Deposition conditions of the EIL may be similar to those for the formation of the HIL, although the conditions may vary depending on a material that is used to form the EIL, in general.

A thickness of the EIL may be in a range from about 1 Å to about 100 Å, or from about 3 Å to about 90 Å. When the thickness of the EIL is within these ranges, the EIL may have satisfactory electron transporting ability without a substantial increase in driving voltage.

The second electrode 17 is disposed on the organic layer 15. The second electrode 17 may be a cathode, which is an electron injecting electrode. A metal for forming the second electrode may be a metal, an alloy, an electrically conductive compound, which have a low-work function, or a mixture thereof. In this regard, the second electrode 17 may be formed of lithium (Li), magnesium (Mg), aluminum (Al), aluminum (Al)-lithium (Li), calcium (Ca), magnesium (Mg)-indium (In), magnesium (Mg)-silver (Ag), or the like, and may be formed as a thin film type transmission electrode. In some embodiments, to manufacture a top-emission light-emitting diode, the transmission electrode may be formed of indium tin oxide (ITO) or indium zinc oxide (IZO).

Hereinbefore, an OLED 10 according to an embodiment has been described with reference to FIG. 1, but is not limited to the structure illustrated in FIG. 1.

In addition, when the EML is formed using a phosphorescent dopant, to prevent diffusion of triplet excitons or holes toward the ETL, a hole blocking layer (HBL) may be formed between the HTL and the EML or between the H-functional layer and the EML by a method, for example, vacuum deposition, spin coating, casting, LB, or the like. When the HBL is formed using vacuum deposition or spin coating, the deposition and coating conditions may be similar to those for the formation of the HIL, though the conditions for deposition and coating may vary depending on the material that is used to form the HBL. Any known hole-blocking material may be used. Examples of hole-blocking materials are oxadiazole derivatives, triazole derivatives, and phenanthroline derivatives. For example, BCP illustrated below may be used as a material for the HBL.

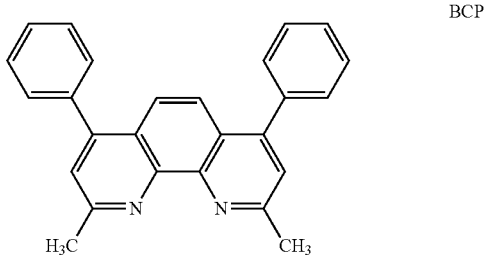 [SMILES: Cc1cc(-c2ccccc2)c2ccc3c(-c4ccccc4)cc(C)nc3c2n1]

BCP

A thickness of the HBL may be in a range from about 20 Å to about 1,000 Å, for example, from about 30 Å to about 300 Å. When the thickness of the HBL is within these ranges, the HBL may have improved hole blocking ability without a substantial increase in driving voltage.

The unsubstituted $C_1$-$C_{60}$ alkyl group (or a $C_1$-$C_{60}$ alkyl group) used herein may be a $C_1$-$C_{60}$ linear or branched alkyl group such as methyl, ethyl, propyl, isobutyl, sec-butyl, pentyl, iso-amyl, or hexyl. The substituted $C_1$-$C_{60}$ alkyl group may be obtained by substituting at least one hydrogen atom of the unsubstituted $C_1$-$C_{60}$ alkyl group with one selected from:

a deuterium atom; —F; —Cl; —Br; —I; —CN; a hydroxyl group; —NO$_2$; an amino group; an amidino group; a hydrazine; a hydrazone; a carboxyl group or a salt thereof; a sulfonic acid or a salt thereof; a phosphoric acid or a salt thereof; tri($C_6$-$C_{60}$aryl)silyl group;

a $C_1$-$C_{60}$ alkyl group, a $C_1$-$C_{60}$ alkoxy group, a $C_2$-$C_{60}$ alkenyl group, and a $C_2$-$C_{60}$ alkynyl group;

a $C_1$-$C_{60}$ alkyl group, a $C_1$-$C_{60}$ alkoxy group, a $C_2$-$C_{60}$ alkenyl group, and a $C_2$-$C_{60}$ alkynyl group, each substituted with at least one of a deuterium atom, —F, —Cl, —Br, —I, —CN, a hydroxyl group, —NO$_2$, an amino group, an amidino group, a hydrazine, a hydrazone, a carboxyl group or a salt thereof, a sulfonic acid or a salt thereof, and a phosphoric acid or a salt thereof;

a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, and a $C_6$-$C_{60}$ arylthio group; and a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, and a $C_6$-$C_{60}$ arylthio group, each substituted with at least one of a deuterium atom, —F, —Cl, —Br, —I, —CN, a hydroxyl group, —NO$_2$, an amino group, an amidino group, a hydrazine, a hydrazone, a carboxyl group or a salt thereof, a sulfonic acid or a salt thereof, a phosphoric acid or a salt thereof, and a $C_1$-$C_{60}$ alkyl group, each substituted with at least one F.

The unsubstituted $C_1$-$C_{60}$ alkoxy group (or $C_1$-$C_{60}$ alkoxy group) used herein has a formula of —OA (where A is the unsubstituted $C_1$-$C_{60}$ alkyl group as described above), and detailed examples thereof are methoxy, ethoxy, and isopropyloxy, and at least one hydrogen atom of these alkoxy groups may be substituted with the same substituent as described above in connection with the substituted $C_1$-$C_{60}$ alkyl group.

The unsubstituted $C_2$-$C_{60}$ alkenyl group (or $C_2$-$C_{60}$ alkenyl group) used herein refers to an unsubstituted $C_2$-$C_{60}$ alkyl group having one or more carbon double bonds at a center or end thereof. Examples of the unsubstituted $C_2$-$C_{60}$ alkenyl group are ethenyl, prophenyl, and butenyl. At least one hydrogen atom of these unsubstituted $C_2$-$C_{60}$ alkenyl groups may be substituted with the same substituent as described above in connection with the substituted $C_1$-$C_{60}$ alkyl group.

The unsubstituted $C_2$-$C_{60}$ alkynyl group (or $C_2$-$C_{60}$ alkynyl group) used herein refers to an unsubstituted $C_2$-$C_{60}$ alkyl group having one or more carbon triple bonds at a center or end thereof. Examples of the unsubstituted $C_2$-$C_{60}$ alkenyl group are ethenyl and prophenyl. At least one hydrogen atom of these unsubstituted $C_2$-$C_{60}$ alkenyl groups may be substituted with the same substituent as described above in connection with the substituted $C_1$-$C_{60}$ alkyl group.

The unsubstituted $C_3$-$C_{60}$ cyclo aryl group used herein refers to a monovalent $C_3$ to $C_{60}$ cyclic saturated, and examples thereof are cyclopropyl, cyclobutyl, cyclopentyl, cyclohexyl, and cycloctyl. At least one hydrogen atom of these cycloalkyl groups may be substituted with the same substituent as described above in connection with the substituted $C_1$-$C_{60}$ alkyl group.

The unsubstituted $C_3$-$C_{60}$ cycloalkenyl group used herein refers to an unsaturated hydrocarbon group having one or more carbon double bonds and being a ring-type group, not an aromatic ring, and examples thereof are cyclopropenyl, cyclobutenyl, cyclopentenyl, cyclohexenyl, cycloheptenyl, a 1,3-cyclohexadienyl group, a 1,4-cyclohexadienyl group, a 2,4-cycloheptadienyl group, and a 1,5-cyclooctadienyl group. At least one hydrogen atom of these cycloalkenyl groups may be substituted with the same substituent as described above in connection with the substituted $C_1$-$C_{60}$ alkyl group.

The unsubstituted $C_6$-$C_{60}$ aryl group used herein is a monovalent group having a carbocyclic aromatic system having 6 to 60 carbon atoms including at least one aromatic ring. The unsubstituted $C_6$-$C_{60}$ arylene group is a divalent group having a carbocyclic aromatic system having 6 to 60 carbon atoms including at least one aromatic ring. When the aryl group and the arylene group include two or more rings, the rings may be fused to each other. At least one hydrogen atom of these aryl groups and arylene groups may be substituted with the same substituent as described above in connection with the substituted $C_1$-$C_{60}$ alkyl group.

Examples of the substituted or unsubstituted $C_6$-$C_{60}$ aryl group are a phenyl group, $C_1$-$C_{10}$ alkylphenyl group (i.e., ethylphenyl group), a $C_1$-$C_{10}$ alkylbiphenyl group (i.e., ethylbiphenyl group), a halophenyl group (i.e., an o-, m-, and p-fluorophenyl group and a dichlorophenyl group), a dicyanophenyl group, a trifluoromethoxyphenyl group, o-, m-, and p-tolyl groups, o-, m- and p-cumenyl groups, a mesityl group, a phenoxyphenyl group, a (α,α-dimethylbenzene)phenyl group, a (N,N-dimethyl)aminophenyl group, a (N,N'-diphenyl)aminophenyl group, a pentalenyl group, an indenyl group, a naphthyl group, a halonaphthyl group (i.e., a fluoronaphthyl group), a C1-C10 alkylnaphthyl group (i.e., a methylnaphthyl group), a C1-C10 alkoxynaphthyl group (i.e., a methoxynaphthyl group), an anthracenyl group, an azrenyl group, a heptalenyl group, an acenaphthylenyl group, a phenalenyl group, a fluorenyl group, an anthraquinolinyl group, a methylanthryl group, a phenanthryl group, a triphenylenyl group, a pyrenyl group, a chrysenyl group, an ethyl-chrysenyl group, a picenyl group, perylenyl group, a chloroperylenyl group, a pentaphenyl group, a pentasenyl group, a tetraphenylenyl group, a hexaphenyl group, a hexacenyl group, a rubicenyl group, a coroneryl group, a trinaphthylenyl group, a heptaphenyl group, a heptacenyl group, a piranthrenyl group, and an obarenyl group, and examples of the substituted $C_6$-$C_{60}$ aryl group may be easily understood by referring to the examples of the unsubstituted $C_6$-$C_{60}$ aryl group and the substituents of the substituted $C_1$-$C_{60}$ alkyl group. Examples of the substituted or unsubstituted $C_6$-$C_{60}$ arylene group may be easily understood by referring to examples of the substituted or unsubstituted $C_6$-$C_{60}$ aryl group.

The unsubstituted $C_2$-$C_{60}$ heteroaryl group used herein refers to a monovalent group having a system composed of one or more aromatic rings having at least one hetero atom selected from nitrogen (N), oxygen (O), phosphorous (P), and sulfur (S) as a ring-forming element, and carbon atoms as the remaining ring atoms. The unsubstituted $C_2$-$C_{60}$ heteroarylene group used herein refers to a divalent group having a system composed of one or more aromatic rings having at least one hetero atom selected from nitrogen (N), oxygen (O), phosphorous (P), and sulfur (S) and carbon atoms as the remaining ring atoms. In this regard, when the heteroaryl group and the heteroarylene group each include two or more rings, the rings may be fused to each other. At least one hydrogen atom of the heteroaryl group and the heteroarylene group may be substituted with the same substituent described in connection with the $C_1$-$C_{60}$ alkyl group.

Examples of the unsubstituted $C_2$-$C_{60}$ heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzo imidazolyl group, an imidazopyridinyl group, and an imidazopyrimidinyl group. Examples of the unsubstituted $C_2$-$C_{60}$ heteroarylene group may be easily understood by referring to the examples of the substituted or unsubstituted $C_2$-$C_{60}$ arylene group.

The substituted or unsubstituted $C_6$-$C_{60}$ aryloxy group indicates —$OA_2$ (where $A_2$ is the substituted or unsubstituted $C_6$-$C_{60}$ aryl group), and the substituted or unsubstituted $C_6$-$C_{60}$ arylthio group indicates —$SA_3$ (where $A_3$ is the substituted or unsubstituted $C_6$-$C_{60}$ aryl group).

Hereinafter, an OLED according to an embodiment is described in detail with reference to Synthesis Examples and Examples. However, the organic light-emitting diode according to an embodiment is not limited to the Synthesis Examples and Examples. For example, the following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples

EXAMPLE

Synthesis Example 1: Synthesis of Complex 2

Synthesis of Intermediate 2(1)

Intermediate 2(1) was synthesized according to Reaction Scheme 1(1):

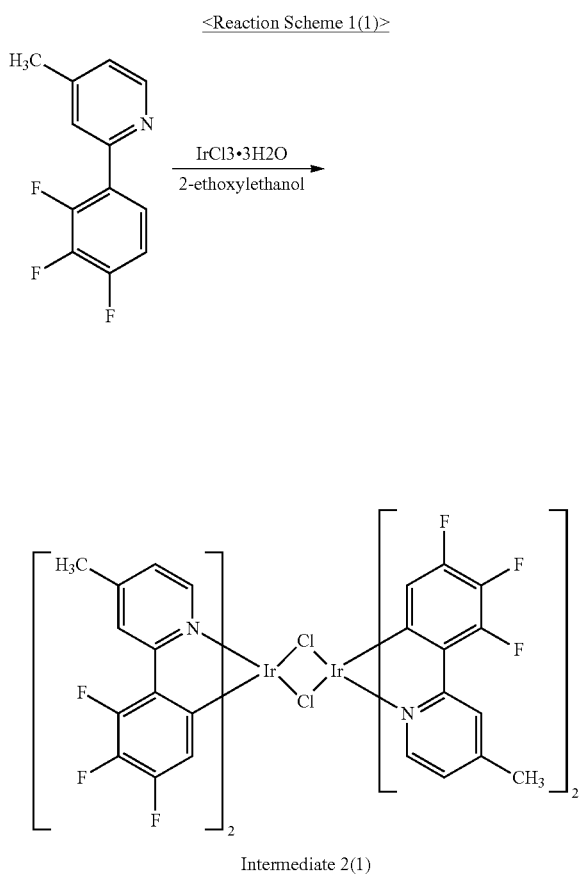

Intermediate 2(1)

3.86 g (17.3 mmol) of 4-methyl-2-(2,3,4-trifluorophenyl)pyridine was dissolved in 45 mL of 2-ethoxyethanol, and 2.4 g (7.6 mmol) of iridium chloride hydrate and 15 mL of distilled water were added thereto, and the mixture was stirred at a temperature of about 130° C. for about 20 hours. After completion of the reaction, the reaction solution was cooled to room temperature and filtered to obtain a precipitate, and the precipitate was washed with methanol and dried in a vacuum condition to obtain 4.3 g of Intermediate 2(1) (Yield 60%).

Synthesis of Complex 2

Complex 2 was synthesized according to Reaction Scheme 1(2):

<Reaction Scheme 1(2)>

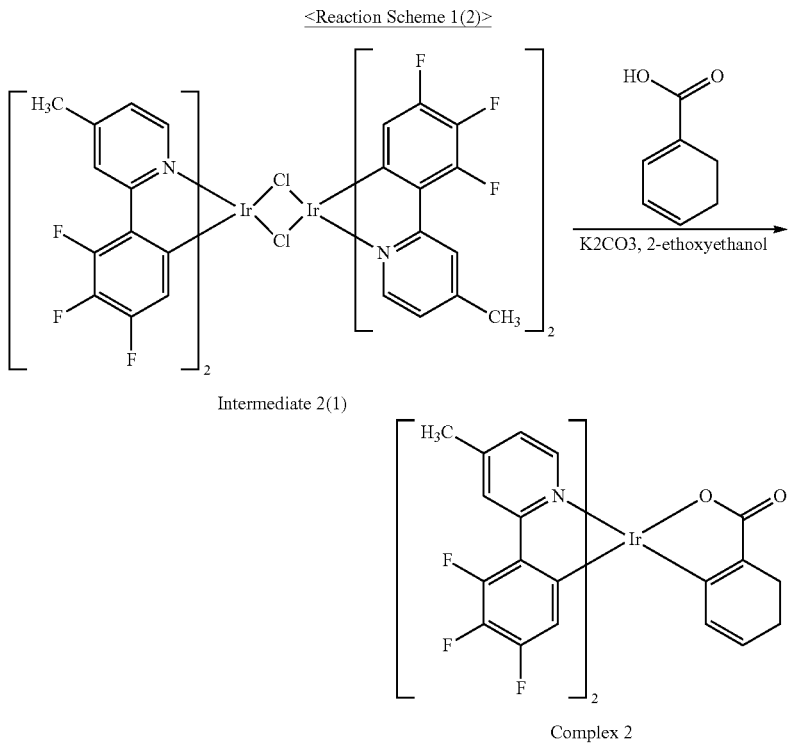

Intermediate 2(1)

Complex 2

1.1 g (1.0 mmol) of Intermediate 2(1), 0.38 g of benzoic acid, and 0.34 g (2.46 mmol) of $K_2CO_3$ were added to 30 mL of 2-ethoxyethanol, and the mixture was stirred at a temperature of about 130° C. for about 12 hours. After completion of the reaction, the reaction solution was cooled to room temperature and filtered to obtain a precipitate, and the precipitate was washed with methanol. The obtained precipitate was dissolved in dichloromethane and filtered through a short pad, and the filtered dichloromethane solution was boiled, and methanol was added in a small amount thereto to obtain 0.60 g of Complex 2 (Yield 53%).

1H-NMR: 8.57 (2H), 8.21 (1H), 7.96 (2H), 7.79 (1H), 7.66 (2H), 7.05 (4H), 2.36 (6H). APCI-MS (m/z): 757[M+]

Synthesis Example 2: Synthesis of Complex 1

Complex 1 was synthesized in the same manner of Synthesis Example 1, except that 2-(2,3,4-trifluorophenyl)pyridine, instead of 4-methyl-2-(2,3,4-trifluorophenyl)pyridine, was used in forming Intermediate 2(1).

1H-NMR: 8.56 (2H), 8.22 (1H), 7.95 (2H), 7.71 (1H), 7.64 (2H), 7.51 (2H), 7.05 APCI-MS (m/z): 729[M+]

Evaluation Example 1: Luminescent Characteristics of Complexes 1 and 2 in Solution The UV absorption spectrum and photoluminescence (PL) spectrum of Complexes 1 and 2 synthesized in Synthesis Example 1 were evaluated to identify luminescent characteristics of Complexes 1 and 2. First, Complex 2 was diluted in toluene to a concentration of 0.2 mM, and an UV absorption spectrum of Complex 2 in solution was measured by using Shimadzu UV-350 Spectrometer, and repeated for Complex 1. Also, Complex 2 was diluted in toluene to a concentration of 10 mM, and a PL spectrum of Complex 2 in solution was measured by using ISC PC1 spectrofluorometer equipped with a Xenon lamp, and results thereof are shown in FIG. 2.

Figure 2:
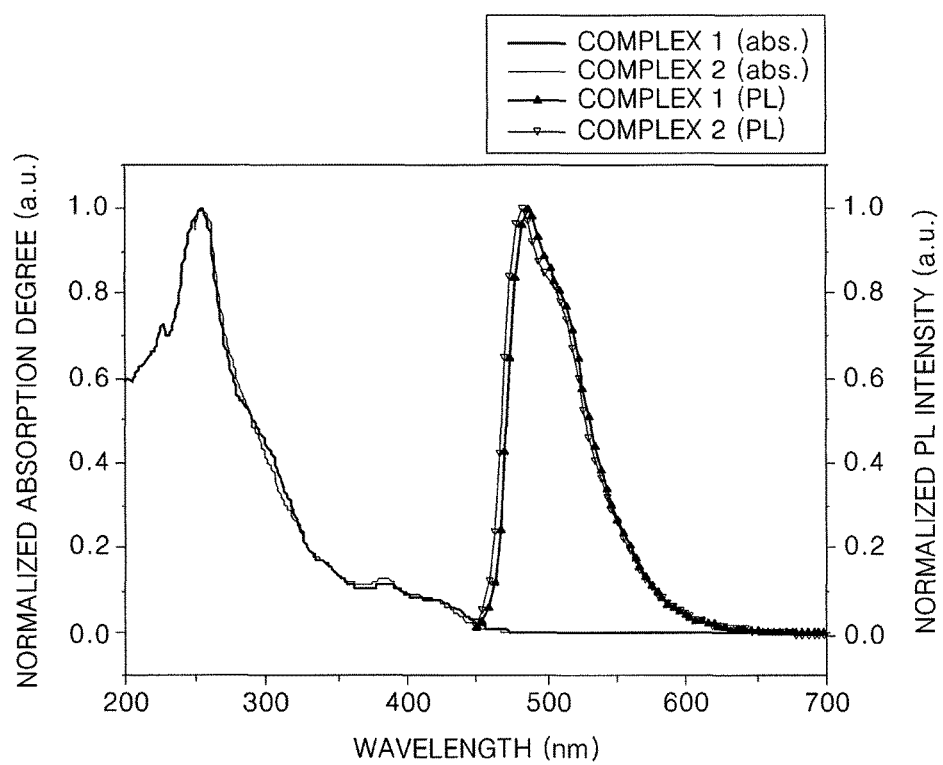
FIG. 2 illustrates a graph showing an ultraviolet (UV) absorption spectrum and PL spectrum of Complexes 1 and 2 in solution.

Referring to FIG. 2, it was confirmed that Complexes 1 and 2 have excellent UV absorption characteristics and PL luminescent characteristics.

Evaluation Example 2: Electric Characteristics of Complexes 1 and 2

Electric characteristics of Complexes 1 and 2 were evaluated by using cyclic voltammetry (CV) (electrolyte: 0.1 M $Bu_4NClO_4$/solvent: $CH_2Cl_2$/electrode: 3 electrode system (working electrode: GC, reference electrode: Ag/AgCl, auxiliary electrode: Pt)), and results thereof are shown in FIG. 3.

Figure 3:
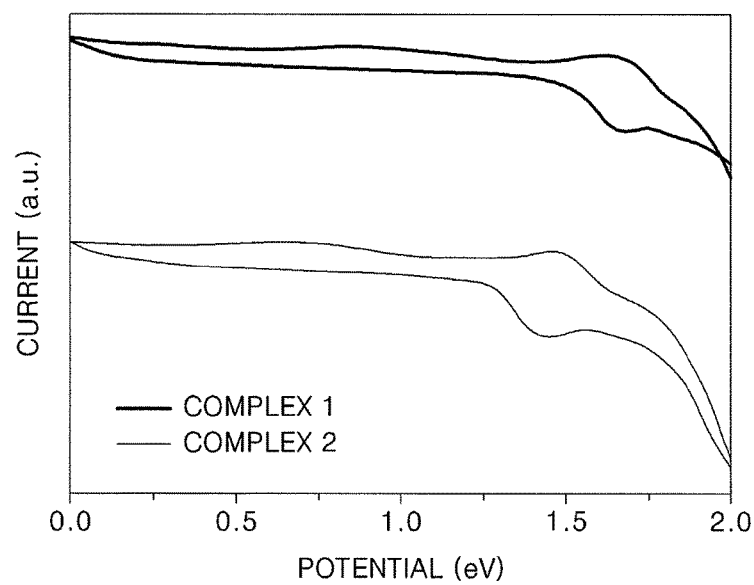
FIG. 3 illustrates a graph showing CV data of Complexes 1 and 2.

From FIG. 3, it was confirmed that Complexes 1 and 2 have electric characteristics suitable for use as a compound for an OLED.

Example 1

An anode was prepared by cutting a corning 15 Ω/cm² (1,200 Å) ITO glass substrate to a size of 50 mm×50 mm×0.7 mm, sonicated in isopropyl alcohol and pure water each for about 5 minutes, and then cleaned by irradiation of UV rays for about 30 minutes and exposure to ozone. Then, the glass substrate was provided into a vacuum deposition apparatus.

PEDOT:PSS was spin coated on the ITO layer and then heat treated at a temperature of about 150° C. to form a hole injection layer having a thickness of 40 nm. PVK (Mw was 25,000), mCP, OXD-7, and Complex 1 were mixed at a weight ratio of 40:27:25:8 (wherein PVK, mCP, and OXD-7 act as a host, and Complex 1 acts as a dopant) and the mixture was spin coated on the hole injection layer and then heat treated at a temperature of about 80° C. to form an emission layer having a thickness of 40 nm. Bphen was deposited on the emission layer to form an electron transport layer having a thickness of 20 nm, and LiF was deposited on the electron transport layer to form an electron injection layer having a thickness of 10 Å, and Al was deposited on the electron injection layer to form a second electrode (cathode) having a thickness of 3,000 Å, thereby completing the manufacturing of an OLED.

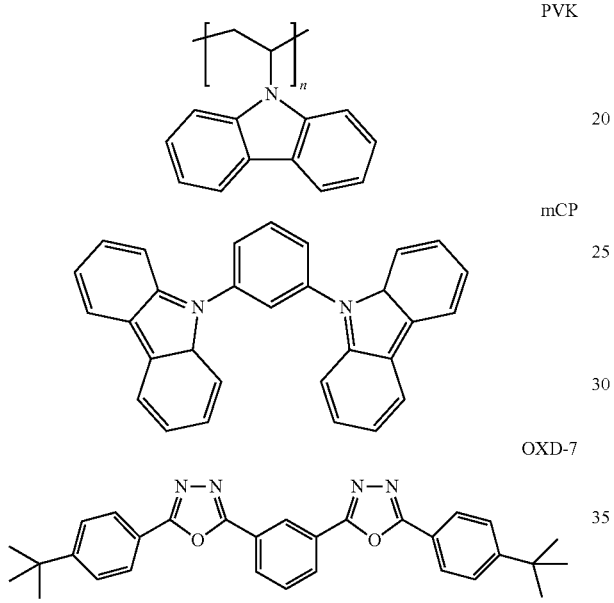

PVK mCP

OXD-7

Example 2

An OLED was manufactured in the same manner as in Example 1, except that Complex 2, instead of Complex 1, was used in forming the emission layer.

Example 3

An anode was prepared by cutting a corning 15 Ω/cm² (1,200 Å) ITO glass substrate to a size of 50 mm×50 mm×0.7 mm, sonicated in isopropyl alcohol and pure water each for about 5 minutes, and then cleaned by irradiation of UV rays for about 30 minutes and exposure to ozone. Then, the glass substrate was provided into a vacuum deposition apparatus.

2-TNATA was deposited on the ITO layer to form a hole injection layer having a thickness of 600 Å, and then, NPB was deposited on the hole injection layer to form an hole transport layer having a thickness of 300 Å. Subsequently, CBP (host) and Complex 1 (dopant) were co-deposited at a weight ratio of 98:2 on the hole transport layer to form an emission layer having a thickness of 400 Å, and then, Compound 101 was deposited on the emission layer to form an electron transport layer having a thickness of 300 Å. LiF was deposited on the electron transport layer to form an electron injection layer having a thickness of 10 Å, and Al was deposited on the electron injection layer to form a second electrode (cathode) having a thickness of 3,000 Å, thereby completing the manufacturing of an OLED

Example 4

An OLED was manufactured in the same manner as in Example 3, except that Complex 2, instead of Complex 1, was used in forming the emission layer.

Comparative Example 1

An OLED was manufactured in the same manner as in Example 3, except that Complex A, instead of Complex 1, was used in forming the emission layer.

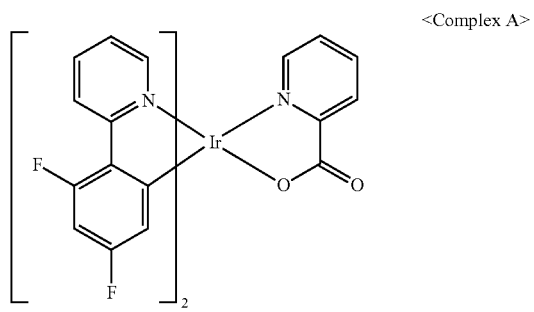

<Complex A>

Comparative Example 2

An OLED was manufactured in the same manner as in Example 3, except that Complex B (Ir(ppy)₃), instead of Complex 1, was used in forming the emission layer.

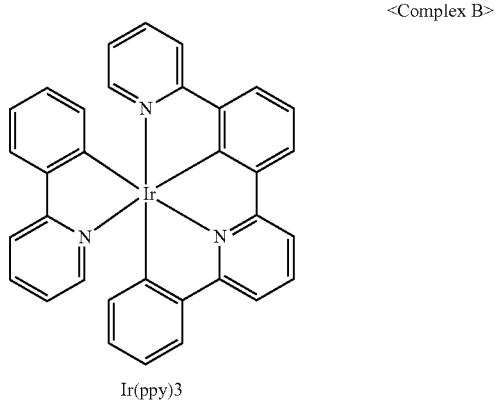

<Complex B>

Ir(ppy)3

Comparative Example 3

An OLED was manufactured in the same manner as in Example 3, except that Complex C, instead of Complex 1, was used in forming the emission layer.

<Complex C>

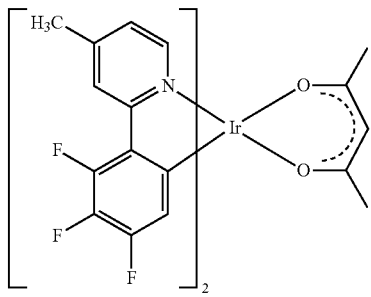

Evaluation Example 3

Efficiency and color purity of the OLEDs of Examples 1 to 4 and Comparative Examples 1 to 3 were evaluated by using PR650 Spectroscan Source Measurement Unit. (a product of PhotoResearch). Results thereof are shown in Table 1 below.

TABLE 1

|  | Dopant | Efficiency (cd/A) at 10 mA/m$^2$ | Color coordinate rate |
|---|---|---|---|
| Example 1 | Complex 1 | 20.1 | 0.18, 0.48 |
| Example 2 | Complex 2 | 21.1 | 0.18, 0.47 |
| Example 3 | Complex 1 | 52.2 | 0.18, 0.48 |
| Example 4 | Complex 2 | 54.7 | 0.18, 0.47 |
| Comparative Example 1 | Complex A | 22.5 | 0.17, 0.35 |
| Comparative Example 2 | Complex B | 32.4 | 0.28, 0.50 |
| Comparative Example 3 | Complex C | 33.5 | 0.20, 0.53 |

Referring to Table 1, it is confirmed that the OLEDs of Examples 1 to 4 have better efficiency and color purities, compared to the OLED of Comparative Examples 1 to 3.

As described above, an organic light-emitting diode including the organometallic complex has high efficiency and high color purity. Accordingly, when the organometallic complex is used, a high-quality light-emitting diode may be embodied.

By way of summation and review, a typical OLED may have a structure including a substrate and an anode on the substrate, and a hole transport layer (HTL), an emission layer (EML), an electron transport layer (ETL), and a cathode that are sequentially stacked on the substrate. In this regard, the HTL, EML, and ETL may be organic thin films formed of organic compounds.

An operating principle of an OLED having the above-described structure is as follows. When a voltage is applied between the anode and cathode, holes injected from the anode move to the EML via the HTL, and electrons injected from the cathode move to the EML via the ETL. Carriers such as the holes and electrons recombine in the EML to generate excitons. When the excitons drop from an excited state to a ground state, light is emitted.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An organometallic complex represented by Formula 1A or 1B below:

<Formula 1A>

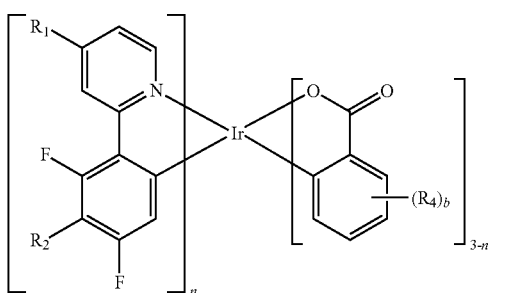

<Formula 1B>

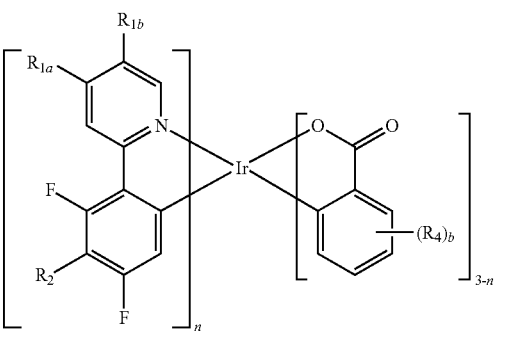

wherein, $R_1$, $R_2$, $R_{1a}$, and $R_{1b}$ are each independently selected from:
a hydrogen atom, a deuterium atom, a halogen atom, a hydroxy group, a cyano group, a nitro group, an amino group, an amidino group, a hydrazine, a hydrazone, a carboxyl group or a salt thereof, a sulfonic acid or a salt thereof, a phosphoric acid or a salt thereof, an unsubstituted $C_1$-$C_{20}$ alkyl group, and an unsubstituted $C_1$-$C_{20}$ alkoxy group;
a $C_1$-$C_{20}$ alkyl group and a $C_1$-$C_{20}$ alkoxy group, each substituted with at least one of a deuterium atom, a halogen atom, a hydroxy group, a cyano group, a nitro group, an amino group, an amidino group, a hydrazine, a hydrazone, a carboxyl group or a salt thereof, a sulfonic acid or a salt thereof, and a phosphoric acid or a salt thereof;
an unsubstituted $C_6$-$C_{14}$ aryl group and an unsubstituted $C_2$-$C_{14}$ heteroaryl group;
a $C_6$-$C_{14}$ aryl group and a $C_2$-$C_{14}$ heteroaryl group, each substituted with at least one of a deuterium atom, a halogen atom, a hydroxy group, a cyano group, a nitro group, an amino group, an amidino group, a hydrazine, a hydrazone, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group, a $C_6$-$C_{14}$ aryl group, and a $C_2$-$C_{14}$ heteroaryl group;
—N($Q_1$)($Q_2$); and
—C(=O)($Q_3$); in which $Q_1$ to $Q_3$ are each independently selected from:
a hydrogen atom, an unsubstituted $C_1$-$C_{20}$ alkyl group, and an unsubstituted $C_1$-$C_{20}$ alkoxy group;
a $C_1$-$C_{20}$ alkyl group and a $C_1$-$C_{20}$ alkoxy group, each substituted with at least one of a deuterium atom, a halogen atom, a hydroxy group, a cyano group, a nitro group, an amino group, an amidino group, a hydrazine, a hydrazone, a carboxyl group or a salt thereof, a sulfonic acid or a salt thereof, and a phosphoric acid or a salt thereof;
an unsubstituted $C_6$-$C_{14}$ aryl group and an unsubstituted $C_2$-$C_{14}$ heteroaryl group; and
a $C_6$-$C_{14}$ aryl group and a $C_2$-$C_{14}$ heteroaryl group, each substituted with at least one of a deuterium atom, a halogen atom, a hydroxy group, a cyano group, a nitro group, an amino group, an amidino group, a hydrazine, a hydrazone, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group, a $C_6$-$C_{14}$ aryl group, and a $C_2$-$C_{14}$ heteroaryl group,
wherein $R_{1a}$ and $R_{1b}$ are separate or are bound to each other to form a saturated or unsaturated ring,
wherein $R_4$ is hydrogen,
wherein b is 4,
wherein n is 1 or 2,
wherein Ir is Ir(III),
wherein the complex includes one potassium ion as a counter ion when n is 2, and wherein the complex includes two potassium ions as counter ions when n is 1.

2. The organometallic complex of claim 1, wherein n is 2.

3. The organometallic complex of claim 1, wherein the organometallic complex is represented by Formula 1A, and $R_1$ in Formula 1A is selected from:
a hydrogen atom, a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonyl group, an isononyl group, a sec-nonyl group, a tert-nonyl group, a n-decanyl group, an isodecanyl group, a sec-decanyl group, a tert-decanyl group, a phenyl group, a naphthyl group, an anthryl group, a pyrenyl group, a phenanthrenyl group, a fluorenyl group, a pyridinyl group, a pyrazinyl group, a pyrimidinyl group, a triazinyl group, a quinolinyl group, an isoquinolinyl group, a quinoxalinyl group, a phenanthrolinyl group, a carbazolyl group, and —N($Q_1$)($Q_2$), in which $Q_1$ and $Q_2$ are each independently selected from:
a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonyl group, an isononyl group, a sec-nonyl group, a tert-nonyl group, a n-decanyl group, an isodecanyl group, a sec-decanyl group, a tert-decanyl group, a phenyl group, a naphthyl group, an anthryl group, a pyrenyl group, a phenanthrenyl group, a fluorenyl group, a pyridinyl group, a pyrazinyl group, a pyrimidinyl group, a triazinyl group, a quinolinyl group, an isoquinolinyl group, a quinoxalinyl group, a phenanthrolinyl group, and a carbazolyl group, and $R_2$ is selected from:
i) F, a cyano group, and a nitro group; and
ii) a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonyl group, an isononyl group, a sec-nonyl group, a tert-nonyl group, a n-decanyl group, an isodecanyl group, a sec-decanyl group, a tert-decanyl group, a phenyl group, a naphthyl group, an anthryl group, a pyrenyl group, a phenanthrenyl group, and a fluorenyl group, each substituted with at least one of F or a $C_1$-$C_{10}$ alkyl group.

4. The organometallic complex of claim 1, wherein the organometallic complex is represented by Formula 1B, and $R_{1a}$ and $R_{1b}$ in Formula 1B are each independently selected from:
a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonyl group, an isononyl group, a sec-nonyl group, a tert-nonyl group, a n-decanyl group, an isodecanyl group, a sec-decanyl group, a tert-decanyl group, a phenyl group, a naphthyl group, an anthryl group, a pyrenyl group, a phenanthrenyl group, a fluorenyl group, a pyridinyl group, a pyrazinyl group, a pyrimidinyl group, a triazinyl group, a quinolinyl group, an isoquinolinyl group, a quinoxalinyl group, a phenanthrolinyl group, a carbazolyl group, and —N($Q_1$)($Q_2$), in which $Q_1$ and $Q_2$ are each independently selected from:
a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonyl group, an isononyl group, a sec-nonyl group, a tert-nonyl group, a n-decanyl group, an isodecanyl group, a sec-decanyl group, a tert-decanyl group, a phenyl group, a naphthyl group, an anthryl group, a pyrenyl group, a phenanthrenyl group, a fluorenyl group, a pyridinyl group, a pyrazinyl group, a pyrimidinyl group, a triazinyl group, a quinolinyl group, an isoquinolinyl group, a quinoxalinyl group, a phenanthrolinyl group, and a carbazolyl group, and $R_2$ is selected from:
i) F, a cyano group, and a nitro group; and
ii) a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonyl group, an isononyl group, a sec-nonyl group, a tert-nonyl group, a n-decanyl group, an isodecanyl group, a sec-decanyl group, a tert-decanyl group, a phenyl group, a naphthyl group, an anthryl group, a pyrenyl group, a phenanthrenyl group, and a fluorenyl group, each substituted with at least one of F or a $C_1$-$C_{10}$ alkyl group.

5. The organometallic complex of claim 1, wherein the organometallic complex is represented by Formula 1B, and $R_{1a}$ and $R_{1b}$ in Formula 1B are each independently selected from:

a phenyl group, a naphthyl group, an anthryl group, a pyrenyl group, a phenanthrenyl group, a fluorenyl group, a pyridinyl group, a pyrazinyl group, a pyrimidinyl group, a triazinyl group, a quinolinyl group, an isoquinolinyl group, a quinoxalinyl group, a phenanthrolinyl group, and a carbazolyl group, and $R_{1a}$ and $R_{1b}$ are bound to each other to form a saturated or unsaturated ring, and $R_2$ is selected from:

i) F, a cyano group, and a nitro group; and ii) a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonyl group, an isononyl group, a sec-nonyl group, a tert-nonyl group, a n-decanyl group, an isodecanyl group, a sec-decanyl group, a tert-decanyl group, a phenyl group, a naphthyl group, an anthryl group, a pyrenyl group, a phenanthrenyl group, and a fluorenyl group, each substituted with at least one of F or a $C_1$-$C_{10}$ alkyl group.

6. An organometallic complex that is one of Complexes 1 to 18 below:

1

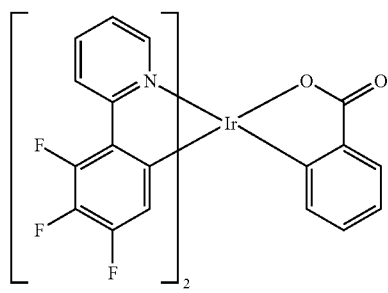

2

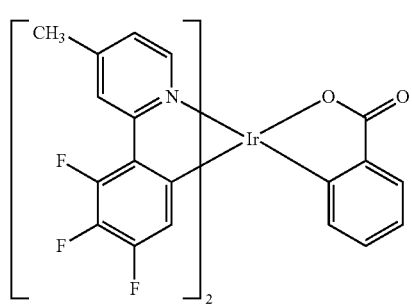

3

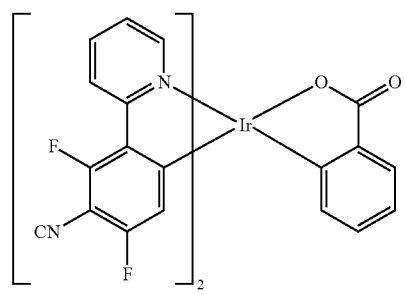

4

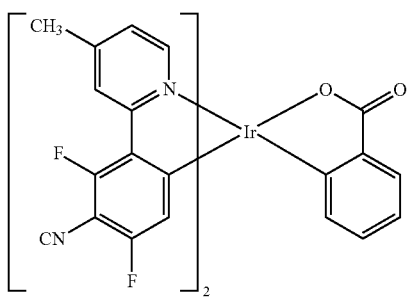

5

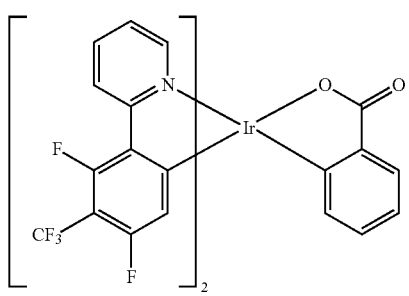

6

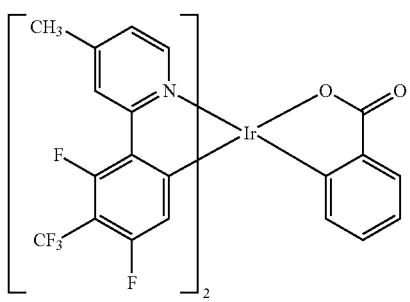

7

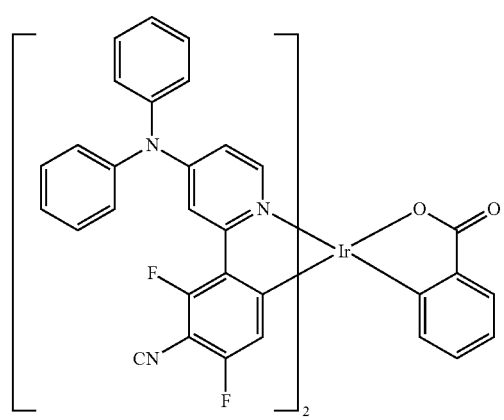

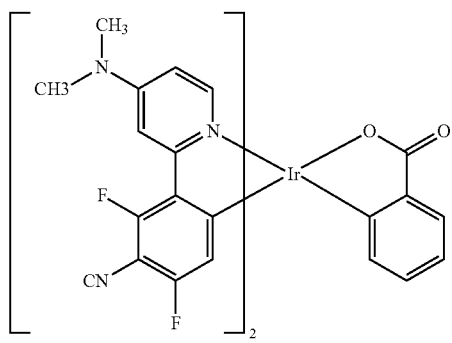
8
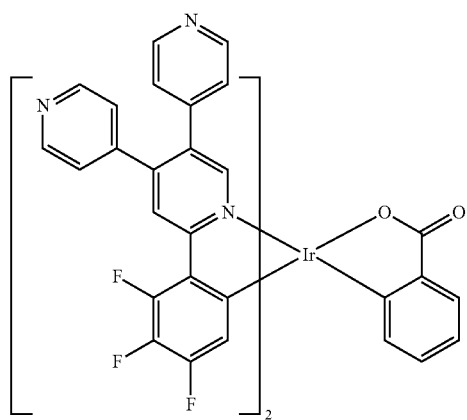
9
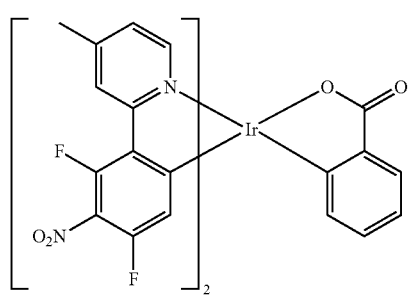
10
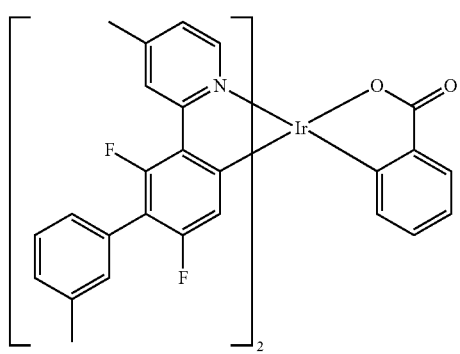
11
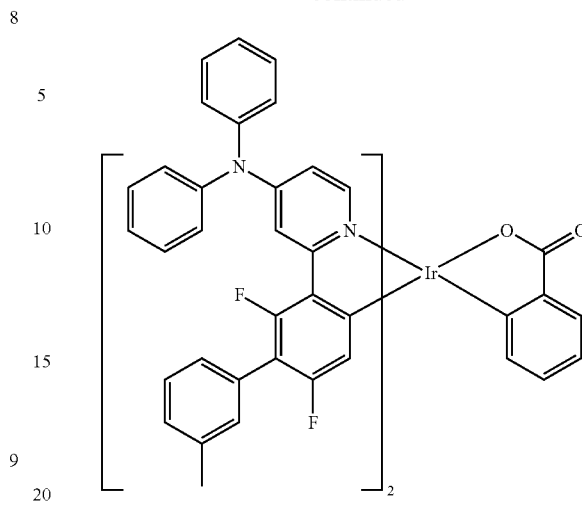
12
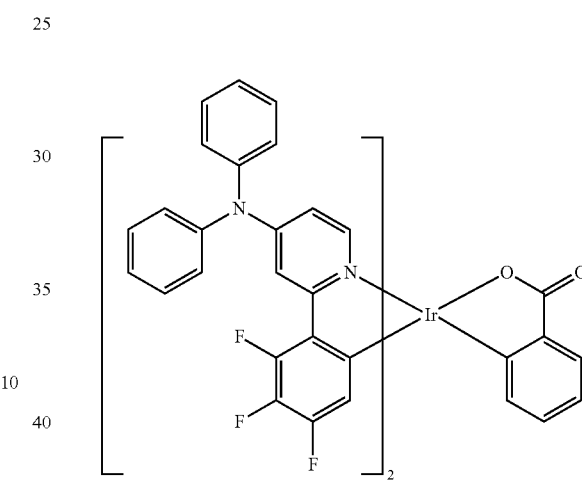
13
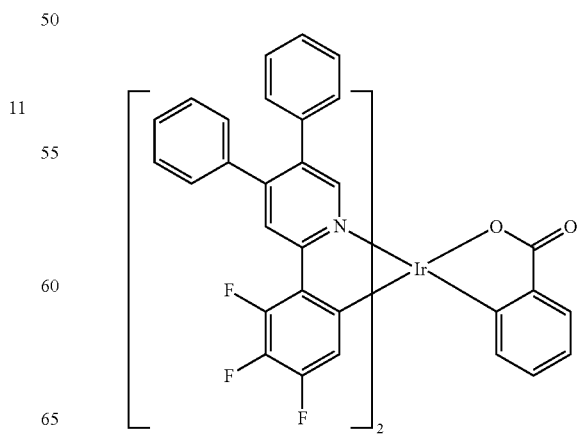
14

15

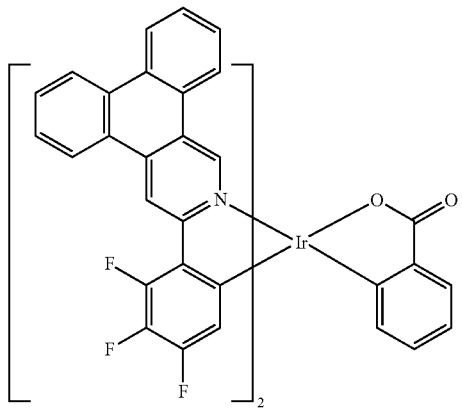

16

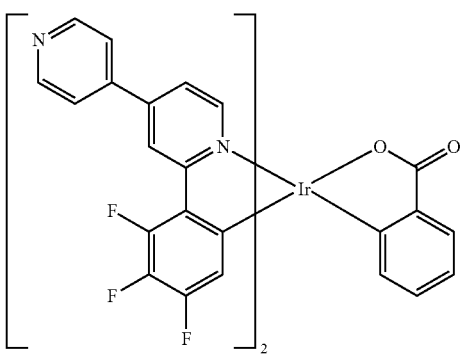

17

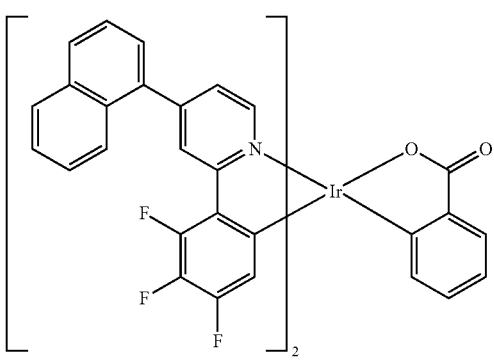

18

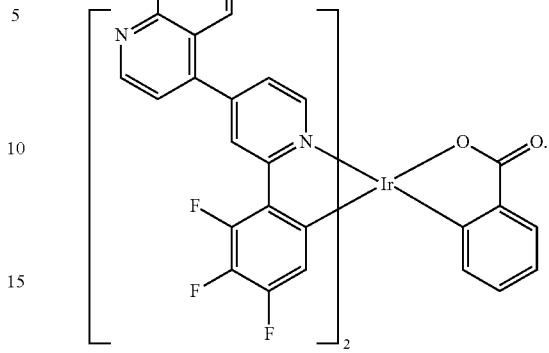

wherein Ir is Ir(III), and
wherein the complex includes one potassium ion as a counter ion.

7. An organic light-emitting diode, comprising:
a first electrode;
a second electrode disposed opposite to the first electrode; and
an organic layer interposed between the first electrode and the second electrode, the organic layer including an emission layer, wherein the organic layer includes one or more organometallic complex as claimed in claim 1.

8. The organic light-emitting diode of claim 7 wherein the organic layer includes:
i) a hole transportation region between the first electrode and the emission layer, the hole transportation region including at least one layer selected from a hole injection layer, a hole transport layer, a functional layer having a hole injection function and a hole transportation function, a buffer layer, and an electron blocking layer, and
ii) an electron transportation region between the emission layer and the second electrode, the electron transportation region including at least one layer selected from a hole blocking layer, an electron transport layer, and an electron injection layer.

9. The organic light-emitting diode of claim 8, wherein the electron transportation region includes an electron transport layer, the electron transport layer including a metal-containing material.

10. The organic light-emitting diode of claim 7, wherein the emission layer includes the organometallic as a phosphorescent dopant, and the emission layer further includes a host.

11. The organic light-emitting diode of claim 7, wherein a concentration of the organometallic complex in the emission layer is in a range of about 0.01 wt % to about 15 wt %, based on 100 wt % of the emission layer.

* * * * *